United States Patent
Nixon et al.

(10) Patent No.: US 10,111,966 B2
(45) Date of Patent: Oct. 30, 2018

(54) METHODS FOR THE DEPLETION OF CD117+ CELLS

(71) Applicant: Magenta Therapeutics, Inc., Cambridge, MA (US)

(72) Inventors: Andrew Nixon, Hanover, MA (US); Dwight Morrow, West Chester, PA (US); Adam Hartigan, Brookline, MA (US)

(73) Assignee: Magenta Therapeutics, Inc., Cambridge, MA (US)

( * ) Notice: Subject to any disclaimer, the term of this patent is extended or adjusted under 35 U.S.C. 154(b) by 0 days.

(21) Appl. No.: 15/626,910

(22) Filed: Jun. 19, 2017

(65) Prior Publication Data

US 2017/0360954 A1   Dec. 21, 2017

Related U.S. Application Data

(60) Provisional application No. 62/448,782, filed on Jan. 20, 2017, provisional application No. 62/437,729, filed on Dec. 22, 2016, provisional application No. 62/351,725, filed on Jun. 17, 2016.

(51) Int. Cl.
| | |
|---|---|
| *A61K 47/68* | (2017.01) |
| *C07K 16/28* | (2006.01) |
| *A61K 35/28* | (2015.01) |

(52) U.S. Cl.
CPC .......... *A61K 47/6849* (2017.08); *A61K 35/28* (2013.01); *A61K 47/6803* (2017.08); *A61K 47/6809* (2017.08); *A61K 47/6811* (2017.08); *A61K 47/6817* (2017.08); *A61K 47/6829* (2017.08); *A61K 47/6831* (2017.08); *C07K 16/2803* (2013.01); *C07K 2317/24* (2013.01); *C07K 2317/565* (2013.01); *C07K 2317/73* (2013.01); *C07K 2317/77* (2013.01); *C07K 2317/92* (2013.01); *C07K 2319/55* (2013.01); *Y02A 50/401* (2018.01); *Y02A 50/414* (2018.01)

(58) Field of Classification Search
None
See application file for complete search history.

(56) References Cited

U.S. PATENT DOCUMENTS

| | | | |
|---|---|---|---|
| 5,273,738 A | 12/1993 | Matthews et al. | |
| 5,378,688 A | 1/1995 | Nett et al. | |
| 5,451,575 A | 9/1995 | Kosuge et al. | |
| 5,489,516 A | 2/1996 | Broudy et al. | |
| 5,548,065 A | 8/1996 | Lemischka | |
| 5,635,388 A | 6/1997 | Bennett et al. | |
| 5,777,084 A | 7/1998 | Buhring | |
| 5,786,457 A | 7/1998 | Nett et al. | |
| 5,808,002 A | 9/1998 | Buhring | |
| 5,906,938 A | 5/1999 | Broudy et al. | |
| 5,919,911 A | 7/1999 | Broudy et al. | |
| 5,922,847 A | 7/1999 | Broudy et al. | |
| 6,099,838 A | 8/2000 | Lazarovits et al. | |
| 6,156,882 A | 12/2000 | Buhring et al. | |
| 6,210,669 B1 | 4/2001 | Aruffo et al. | |
| 6,339,062 B1 | 1/2002 | Williams et al. | |
| 7,160,987 B2 | 1/2007 | Lazarovits et al. | |
| 7,183,385 B2 | 2/2007 | Comb et al. | |
| 7,265,212 B2 | 9/2007 | Babcook et al. | |
| 7,825,222 B2 | 11/2010 | Aversa et al. | |
| 7,915,391 B2 | 3/2011 | Ng et al. | |
| 8,071,099 B2 | 12/2011 | Li et al. | |
| 8,436,150 B2 | 5/2013 | Ng et al. | |
| 8,791,249 B2 | 7/2014 | Ng et al. | |
| 8,821,867 B2 | 9/2014 | Ahrens et al. | |
| 9,023,996 B2 | 5/2015 | Grosse-Hovest et al. | |
| 9,109,227 B2 | 8/2015 | Valmier | |
| 9,540,443 B2 | 1/2017 | Hadari et al. | |
| 2002/0018775 A1 | 2/2002 | Broudy et al. | |

(Continued)

FOREIGN PATENT DOCUMENTS

| | | |
|---|---|---|
| CN | 1341362 A | 3/2002 |
| CN | 101861796 A | 10/2010 |

(Continued)

OTHER PUBLICATIONS

Holliger and Hudson, Nature Biotechnology, 2005, vol. 23, pp. 1126-1136 (Year: 2005).*
Hamblett et al (Clinical Cancer Research, 2004, vol. 10, pp. 7063-7070) (Year: 2004).*
Abstract of Reis et al (Blood, 2015, vol. 126, No. 23, p. 2580). (Year: 2015).*
Bougherara et al., "The aberrant localization of oncogenic kit tyrosine kinase receptor mutants is reversed on specific inhibitory treatment," Mol Cancer Res. 7(9):1525-33 (2009) (10 pages).
Chandrasekaran et al., "Modeling promising nonmyeloablative conditioning regimens in nonhuman primates," Hum Gene Ther. 25(12):1013-22 (2014).

(Continued)

*Primary Examiner* — Karen A. Canella
(74) *Attorney, Agent, or Firm* — Womble Bond Dickinson (US) LLP; Cristin H. Cowles; Kevin A. Fiala

(57) ABSTRACT

The invention provides compositions and methods useful for the depletion of CD117+ cells and for the treatment of various hematopoietic diseases, metabolic disorders, cancers, and autoimmune diseases, among others. Described herein are antibodies, antigen-binding fragments, ligands, and conjugates thereof that can be applied to effect the treatment of these conditions, for instance, by depleting a population of CD117+ cells in a patient, such as a human. The compositions and methods described herein can be used to treat a disorder directly, for instance, by depleting a population of CD117+ cancer cells or autoimmune cells. The compositions and methods described herein can also be used to prepare a patient for hematopoietic stem cell transplant therapy and to improve the engraftment of hematopoietic stem cell transplants by selectively depleting endogenous hematopoietic stem cells prior to the transplant procedure.

16 Claims, 5 Drawing Sheets

Specification includes a Sequence Listing.

(56) References Cited

U.S. PATENT DOCUMENTS

| | | |
|---|---|---|
| 2003/0093819 A1 | 5/2003 | D'Andrea et al. |
| 2003/0232369 A1 | 12/2003 | Bushnell et al. |
| 2006/0014197 A1 | 1/2006 | Landick |
| 2008/0003224 A1 | 1/2008 | Fong et al. |
| 2009/0054358 A1 | 2/2009 | Small et al. |
| 2010/0093008 A1 | 4/2010 | Goss et al. |
| 2010/0226927 A1 | 9/2010 | Weissman et al. |
| 2010/0267019 A1 | 10/2010 | Hallen et al. |
| 2011/0177104 A1 | 7/2011 | Kwon et al. |
| 2012/0288506 A1 | 11/2012 | Amatulli et al. |
| 2013/0288373 A1 | 10/2013 | Verstraete et al. |
| 2014/0271688 A1 | 9/2014 | Abrams et al. |
| 2015/0018408 A1 | 1/2015 | Lukacs et al. |
| 2015/0320880 A1 | 11/2015 | Abrams et al. |
| 2016/0220687 A1 | 8/2016 | Alhamdan |
| 2016/0264680 A1 | 9/2016 | Poul et al. |
| 2016/0272716 A1 | 9/2016 | Lowe et al. |
| 2016/0311924 A1 | 10/2016 | Hadari et al. |
| 2017/0021033 A1 | 1/2017 | Geierstanger et al. |
| 2017/0035905 A1 | 2/2017 | Abrams et al. |
| 2017/0158778 A1 | 6/2017 | Hadari et al. |

FOREIGN PATENT DOCUMENTS

| | | |
|---|---|---|
| CN | 102526034 A | 7/2012 |
| CN | 102786586 A | 11/2012 |
| CN | 103627757 A | 3/2014 |
| CN | 104862314 A | 8/2015 |
| CN | 105177009 A | 12/2015 |
| CN | 106153768 A | 11/2016 |
| DE | 4343261 A1 | 6/1995 |
| DE | 10219866 A1 | 11/2003 |
| EP | 939125 A2 | 9/1999 |
| EP | 1661584 A1 | 5/2006 |
| EP | 1859811 A1 | 11/2007 |
| GB | 2282812 A | 4/1995 |
| WO | WO-93/15751 A1 | 8/1993 |
| WO | WO-94/25621 A1 | 11/1994 |
| WO | WO-95/07348 A1 | 3/1995 |
| WO | WO-95/13093 A1 | 5/1995 |
| WO | WO-98/46264 A1 | 10/1998 |
| WO | WO-00/61775 A1 | 10/2000 |
| WO | WO-00/66090 A1 | 11/2000 |
| WO | WO-00/66091 A1 | 11/2000 |
| WO | WO-00/66182 A1 | 11/2000 |
| WO | WO-02/32955 A1 | 4/2002 |
| WO | WO-02/088354 A1 | 11/2002 |
| WO | WO-03/026641 A2 | 4/2003 |
| WO | WO-03/051311 A2 | 6/2003 |
| WO | WO-2004/002425 A2 | 1/2004 |
| WO | WO-2004/045647 A1 | 6/2004 |
| WO | WO-2004/058165 A2 | 7/2004 |
| WO | WO-2006/002064 A2 | 1/2006 |
| WO | WO-2006/127978 A2 | 11/2006 |
| WO | WO-2007/080114 A2 | 7/2007 |
| WO | WO-2007/121326 A2 | 10/2007 |
| WO | WO-2007/127317 A2 | 11/2007 |
| WO | WO-2008/067115 A2 | 6/2008 |
| WO | WO-2009/002993 A1 | 12/2008 |
| WO | WO-2009/011893 A2 | 1/2009 |
| WO | WO-2010/045218 A1 | 4/2010 |
| WO | WO-2010/081015 A1 | 7/2010 |
| WO | WO-2010/115629 A2 | 10/2010 |
| WO | WO-2010/115630 A1 | 10/2010 |
| WO | WO-2011/078665 A1 | 6/2011 |
| WO | WO-2012/041504 A1 | 4/2012 |
| WO | WO-2012/047317 A2 | 4/2012 |
| WO | WO-2012/047354 A2 | 4/2012 |
| WO | WO-2012/119787 A1 | 9/2012 |
| WO | WO-2013/131927 A1 | 9/2013 |
| WO | WO-2013/173391 A1 | 11/2013 |
| WO | WO-2013/173392 A1 | 11/2013 |
| WO | WO-2013/173393 A1 | 11/2013 |
| WO | WO-2013/192546 A1 | 12/2013 |
| WO | WO-2014/009025 A1 | 1/2014 |
| WO | WO-2014/043403 A1 | 3/2014 |
| WO | WO-2014/044872 A1 | 3/2014 |
| WO | WO-2014/049366 A1 | 4/2014 |
| WO | WO-2014/062697 A2 | 4/2014 |
| WO | WO-2014/102299 A2 | 7/2014 |
| WO | WO-2014/135282 A1 | 9/2014 |
| WO | WO-2014/150937 A1 | 9/2014 |
| WO | WO-2014208987 A1 | 12/2014 |
| WO | WO-2015/013429 A1 | 1/2015 |
| WO | WO-2015005431 A1 | 1/2015 |
| WO | WO-2015/050959 A1 | 4/2015 |
| WO | WO-2016/001485 A1 | 1/2016 |
| WO | WO-2016/014839 A2 | 1/2016 |
| WO | WO-2016/033201 A1 | 3/2016 |
| WO | WO-2016/036334 A1 | 3/2016 |
| WO | WO-2016/059622 A2 | 4/2016 |
| WO | WO-2016/061509 A1 | 4/2016 |
| WO | WO-2016/071856 A1 | 5/2016 |
| WO | WO-2016/077505 A2 | 5/2016 |
| WO | WO-2016/131769 A2 | 8/2016 |
| WO | WO-2016/141185 A1 | 9/2016 |
| WO | WO-2016/142049 A1 | 9/2016 |
| WO | WO-2016/145014 A1 | 9/2016 |
| WO | WO-2016/154588 A1 | 9/2016 |
| WO | WO-2016/164502 A1 | 10/2016 |
| WO | WO-2016/164745 A1 | 10/2016 |
| WO | WO-2016/168471 A1 | 10/2016 |
| WO | WO-2016/185403 A1 | 11/2016 |
| WO | WO-2016/191186 A1 | 12/2016 |
| WO | WO-2016/205738 A2 | 12/2016 |
| WO | WO-2017/004127 A1 | 1/2017 |
| WO | WO-2017/009473 A1 | 1/2017 |
| WO | WO-2017/011803 A1 | 1/2017 |
| WO | WO-2017/023753 A1 | 2/2017 |

OTHER PUBLICATIONS

Czechowicz et al., "Efficient transplantation via antibody-based clearance of hematopoietic stem cell niches," Science 318(5854):1296-9 (8 pages) (2007).

Derderian et al., "In utero depletion of fetal hematopoietic stem cells improves engraftment after neonatal transplantation in mice," Blood 124(6):973-80 (2014).

First Examination Report for Australian Patent Application No. 2017204125, dated Aug. 24, 2017 (9 pages).

First Examination Report for Australian Patent Application No. 2017204139, dated Aug. 1, 2017 (6 pages).

Matthews et al., "Radiolabeled Anti-CD45 Monoclonal Antibodies Target Lymphohematopoietic Tissue in the Macaque", Blood 78(7):1864-74 (1991).

Merlini et al., "Studies on c-KIT protein expression and c-KIT gene mutation in multiple myeloma," Haematologica 94, Suppl. 4, P084: 87 (2009).

Palchaudhuri et al., "Non-genotoxic conditioning for hematopoietic stem cell transplantation using a hematopoietic-cell-specific internalizing immunotoxin," Nat Biotechnol. 34(7):738-45 (22 pages) (2016).

International Search Report for PCT/US2017/038158, 8 pages.

* cited by examiner

SEQUENCE LISTING

```
<160> NUMBER OF SEQ ID NOS: 8

<210> SEQ ID NO 1
<211> LENGTH: 5
<212> TYPE: PRT
<213> ORGANISM: Homo sapiens

<400> SEQUENCE: 1

Ser Tyr Trp Ile Gly
1               5

<210> SEQ ID NO 2
<211> LENGTH: 17
<212> TYPE: PRT
<213> ORGANISM: Homo sapiens

<400> SEQUENCE: 2

Ile Ile Tyr Pro Gly Asp Ser Asp Thr Arg Tyr Ser Pro Ser Phe Gln
1               5                   10                  15

Gly

<210> SEQ ID NO 3
<211> LENGTH: 14
<212> TYPE: PRT
```

<213> ORGANISM: Homo sapiens

<400> SEQUENCE: 3

His Gly Arg Gly Tyr Asn Gly Tyr Glu Gly Ala Phe Asp Ile
1               5                   10

<210> SEQ ID NO 4
<211> LENGTH: 11
<212> TYPE: PRT
<213> ORGANISM: Homo sapiens

<400> SEQUENCE: 4

Arg Ala Ser Gln Gly Ile Ser Ser Ala Leu Ala
1               5                   10

<210> SEQ ID NO 5
<211> LENGTH: 7
<212> TYPE: PRT
<213> ORGANISM: Homo sapiens

<400> SEQUENCE: 5

Asp Ala Ser Ser Leu Glu Ser
1               5

<210> SEQ ID NO 6
<211> LENGTH: 10
<212> TYPE: PRT
<213> ORGANISM: Homo sapiens

<400> SEQUENCE: 6

Cys Gln Gln Phe Asn Ser Tyr Pro Leu Thr
1               5                   10

<210> SEQ ID NO 7
<211> LENGTH: 120
<212> TYPE: PRT
<213> ORGANISM: Homo sapiens

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Ala Met Ser Trp Val Arg Gln Ala Pro Gly Lys Gly Leu Glu Trp Val
        35                  40                  45

Ala Val Ile Ser Glu Asn Gly Ser Asp Thr Tyr Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Arg Gly Gly Ala Val Ser Tyr Phe Asp Val Trp Gly Gln
            100                 105                 110

```
Gly Thr Leu Val Thr Val Ser Ser
        115                 120

<210> SEQ ID NO 8
<211> LENGTH: 109
<212> TYPE: PRT
<213> ORGANISM: Homo sapiens

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Tyr
            20                  25                  30

Leu Ala Trp Tyr Gln Gln Lys Pro Gly Lys Ala Pro Lys Leu Leu Ile
        35                  40                  45

Tyr Ala Ala Ser Ser Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Leu Pro Tyr
                85                  90                  95

Thr Phe Gly Gln Gly Thr Lys Val Glu Ile Lys Arg Thr
            100                 105
```

METHODS FOR THE DEPLETION OF CD117+ CELLS

FIELD OF THE INVENTION

The invention relates to the treatment of patients suffering from various pathologies, such as blood diseases, metabolic disorders, cancers, and autoimmune diseases, among others, by administration of an antibody, antigen-binding fragment thereof, or ligand capable of binding an antigen expressed by a hematopoietic cell, such as a hematopoietic stem cell.

BACKGROUND OF THE INVENTION

Despite advances in the medicinal arts, there remains a demand for treating pathologies of the hematopoietic system, such as diseases of a particular blood cell, metabolic disorders, cancers, and autoimmune conditions, among others. While hematopoietic stem cells have significant therapeutic potential, a limitation that has hindered their use in the clinic has been the difficulty associated with ensuring engraftment of hematopoietic stem cell transplants in a host. There is currently a need for compositions and methods for promoting the engraftment of exogenous hematopoietic stem cell grafts such that the multi-potency and hematopoietic functionality of these cells is preserved following transplantation.

SUMMARY OF THE INVENTION

The present invention provides compositions and methods for the direct treatment of various disorders of the hematopoietic system, metabolic disorders, cancers, and autoimmune diseases, among others. The invention additionally features methods for conditioning a patient, such as a human patient, prior to receiving hematopoietic stem cell transplant therapy so as to promote the engraftment of hematopoietic stem cell grafts. The patient may be one that is suffering from one or more blood disorders, such as a hemoglobinopathy or other hematopoietic pathology, and is thus in need of hematopoietic stem cell transplantation. As described herein, hematopoietic stem cells are capable of differentiating into a multitude of cell types in the hematopoietic lineage, and can be administered to a patient in order to populate or re-populate a cell type that is deficient in the patient. The invention features methods of treating a patient with antibodies and drug-antibody conjugates capable of binding proteins expressed by hematopoietic cells, such as CD117 (including, for example, GNNK+ CD117), so as to (i) directly treat a disease such as a blood disorder, metabolic disease, cancer, or autoimmune disease, among others described herein, by selectively depleting a population of cells that express CD117, such as an aberrant blood cell, cancer cell, or autoimmune cell, and/or (ii) deplete a population of endogenous hematopoietic stem cells within the patient. The former activity enables the direct treatment of a wide range of disorders associated with a cell of the hematopoietic lineage, as CD117 may be expressed by a cancerous cell, such as a leukemic cell, an autoimmune lymphocyte, such as a T-cell that expresses a T-cell receptor that cross-reacts with a self antigen, among other cell types. The latter activity, the selective depletion of hematopoietic stem cells, in turn creates a vacancy that can subsequently be filled by transplantation of an exogenous (for instance, an autologous, allogeneic, or syngeneic) hematopoietic stem cell graft. The invention thus provides methods of treating a variety of hematopoietic conditions, such as sickle cell anemia, thalassemia, Fanconi anemia, Wiskott-Aldrich syndrome, adenosine deaminase deficiency-severe combined immunodeficiency, metachromatic leukodystrophy, Diamond-Blackfan anemia and Schwachman-Diamond syndrome, human immunodeficiency virus infection, and acquired immune deficiency syndrome, as well as cancers and autoimmune diseases, among others.

In a first aspect, the invention provides a method of depleting a population of CD117+ cells in a human patient by administering an effective amount of an antibody or antigen-binding fragment thereof capable of binding CD117 conjugated to a cytotoxin.

In another aspect, the invention provides a method of depleting a population of CD117+ cells in a human patient in need of a hematopoietic stem cell transplant by administering, prior to the patient receiving a transplant including hematopoietic stem cells, an effective amount of an antibody or antigen-binding fragment thereof capable of binding CD117 conjugated to a cytotoxin.

In another aspect, the invention features a method, for example, of treating a human patient in need of a hematopoietic stem cell transplant, including administering to a human patient a transplant including hematopoietic stem cells, wherein the patient has been previously administered an antibody or antigen-binding fragment thereof capable of binding CD117 conjugated to a cytotoxin in an amount sufficient to deplete a population of CD117+ cells in the patient.

In an additional aspect, the invention features a method, for example, of treating a human patient in need of a hematopoietic stem cell transplant, including: administering to a human patient an antibody or antigen-binding fragment thereof capable of binding CD117 conjugated to a cytotoxin in an amount sufficient to deplete a population of CD117+ cells in the patient, and subsequently administering to the patient a transplant including hematopoietic stem cells.

In some embodiments of any of the foregoing aspects of the invention, the antibody or antigen-binding fragment thereof is conjugated to a cytotoxin.

In any of the above aspects, the cytotoxin may be, for example, pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, or a variant thereof.

In some embodiments of any of the above aspects, the CD117 is GNNK+CD117.

In another aspect, the invention provides a method of depleting a population of CD117+ cells in a human patient by administering an effective amount of a ligand or fragment thereof capable of binding CD117.

In another aspect, the invention provides a method of depleting a population of CD117+ cells in a human patient in need of a hematopoietic stem cell transplant by administering, prior to the patient receiving a transplant including hematopoietic stem cells, an effective amount of a ligand or fragment thereof capable of binding CD117.

In another aspect, the invention features a method, for example, of treating a human patient in need of a hematopoietic stem cell transplant, including administering to a human patient a transplant including hematopoietic stem cells, wherein the patient has been previously administered a ligand or fragment thereof capable of binding CD117 in an amount sufficient to deplete a population of CD117+ cells in the patient.

In an additional aspect, the invention features a method, for example, of treating a human patient in need of a hematopoietic stem cell transplant, including: administering to a human patient a ligand or fragment thereof capable of binding CD117 in an amount sufficient to deplete a population of CD117+ cells in the patient, and subsequently administering to the patient a transplant including hematopoietic stem cells.

In some embodiments of any of the preceding four aspects, the ligand or fragment thereof that binds CD117 (e.g., GNNK+CD117) is covalently bound to an Fc domain, such as a dimeric Fc domain isolated from a human antibody (for example, isolated from an IgG1, IgG2, IgG3, or IgG4 isotype human antibody). In some embodiments, the Fc domain is a monomeric Fc domain containing a single polypeptide strand. In some embodiments, the N-terminus of the ligand or fragment thereof is bound to the Fc domain. In some embodiments, the C-terminus of the ligand or fragment thereof is bound to the Fc domain. The Fc domain may be conjugated to one or more copies of the ligand or fragment thereof. For instance, conjugates that may be used with the methods described herein include dimeric Fc domains in which each polypeptide strand of the Fc domain is conjugated to the ligand or fragment thereof. The Fc domain may in turn be conjugated to a cytotoxin, such as a cytotoxin described herein (for example, pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

In some embodiments of the preceding four aspects, the ligand or fragment thereof is covalently bound to a cytotoxin, such as a cytotoxin described herein (for example, pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof). In some embodiments, the N-terminus of the ligand or fragment thereof is bound to the cytotoxin. In some embodiments, the C-terminus of the ligand or fragment thereof is bound to the cytotoxin. The cytotoxin may in turn be conjugated to an Fc domain.

In some embodiments, the ligand or fragment thereof is covalently bound to the cytotoxin at one site on the ligand or fragment thereof (for example, the N- or C-terminus of the ligand or fragment thereof) and is covalently bound to an Fc domain at another site on the ligand or fragment thereof (for example, the opposite terminus of the ligand or fragment thereof).

In some embodiments, the Fc domain is a human IgG1 isotype Fc domain. In some embodiments, the Fc domain is a human IgG2 isotype Fc domain. In some embodiments, the Fc domain is a human IgG3 isotype Fc domain. In some embodiments, the Fc domain is a human IgG4 isotype Fc domain.

In some embodiments of any of the above aspects, the cytotoxin is an amatoxin or derivative thereof, such as α-amanitin, β-amanitin, γ-amanitin, ε-amanitin, amanin, amaninamide, amanullin, amanullinic acid, and proamanullin. In some embodiments of any of the above aspects, the cytotoxin is an amatoxin, and the antibody, antigen-binding fragment thereof, or ligand conjugated to the cytotoxin is represented by the formula Ab-Am, wherein Ab is the antibody, antigen-binding fragment thereof, or ligand, and Am is the amatoxin. In some embodiments, Am is represented by formula (I)

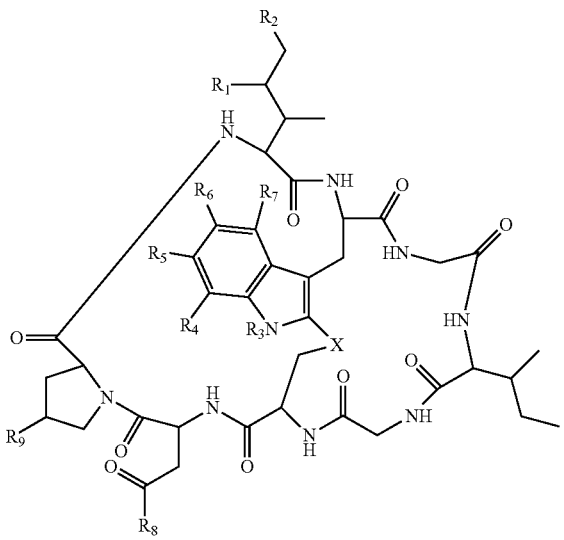

(I)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocyclolalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene; and
Z is a chemical moiety formed from a coupling reaction between a reactive substituent present on L and a reactive substituent present within an antibody, antigen-binding fragment thereof, or ligand that binds CD117 (such as GNNK+CD117).

In some embodiments, Am contains exactly one $R_C$ substituent.

In some embodiments, Am is represented by formula (IA)

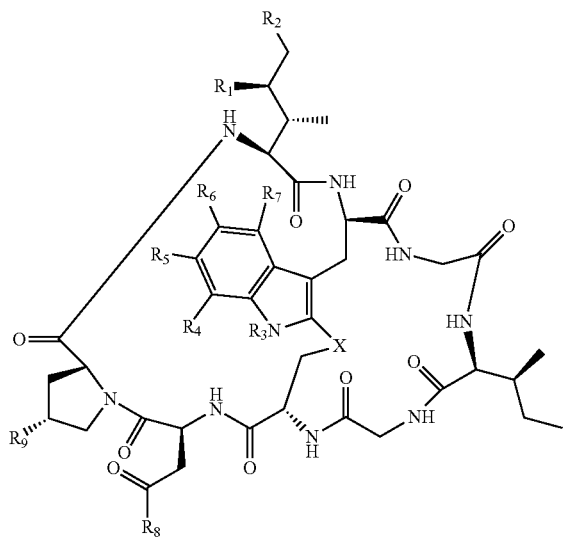

(IA)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocyclolalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene;
Z is a chemical moiety formed from a coupling reaction between a reactive substituent present on L and a reactive substituent present within an antibody, antigen-binding fragment thereof, or ligand that binds CD117 (such as GNNK+ CD117); and
wherein Am contains exactly one $R_C$ substituent.

In some embodiments, Am is represented by formula (IB)

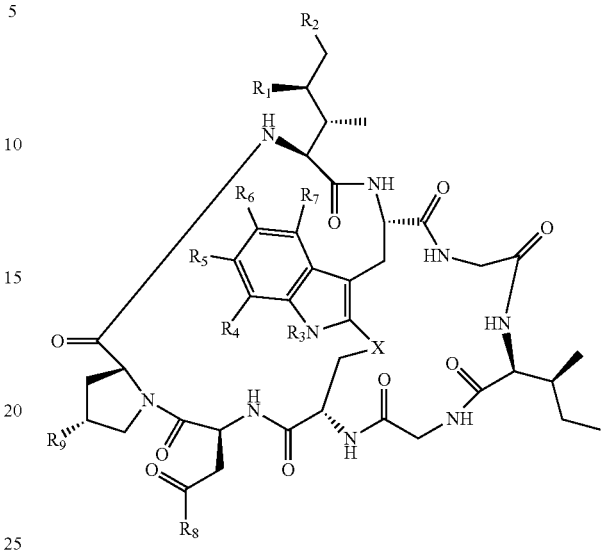

(IB)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocyclolalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene;
Z is a chemical moiety formed from a coupling reaction between a reactive substituent present on L and a reactive substituent present within an antibody, antigen-binding fragment thereof, or ligand that binds CD117 (such as GNNK+ CD117); and
wherein Am contains exactly one $R_C$ substituent.

In some embodiments, $R_A$ and $R_B$, together with the oxygen atoms to which they are bound, combine to form:

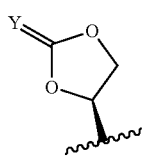

wherein Y is selected from O, S, $NR_E$, and $CR_ER_{E'}$, and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am is represented by formula (IA) or formula (IB), wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form:

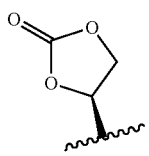 [SMILES: *[C@@H]1COC(=O)O1]

$R_3$ is H or $R_C$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, or $NHR_C$;
$R_9$ is H or OH; and
wherein $R_C$ and $R_D$ are each as defined above.

In some embodiments, Am is represented by formula (IA) or formula (IB),
wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form:

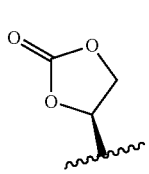 [SMILES: *[C@@H]1COC(=O)O1]

$R_3$ is H or $R_C$;
$R_4$ and $R_5$ are each independently H, OH, $OR_C$, $R_C$, or $OR_D$;
$R_6$ and $R_7$ are each H;
$R_8$ is OH, $NH_2$, $OR_C$, or $NHR_C$;
$R_9$ is H or OH; and
wherein $R_C$ is as defined above.

In some embodiments, Am is represented by formula (IA) or formula (IB),
wherein $R_1$ is H, OH, or $OR_A$;
$R_2$ is H, OH, or $OR_B$;
$R_A$ and $R_B$, together with the oxygen atoms to which they are bound, combine to form:

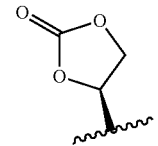 [SMILES: *[C@@H]1COC(=O)O1]

$R_3$, $R_4$, $R_6$, and $R_7$ are each H;
$R_5$ is $OR_C$;
$R_8$ is OH or $NH_2$;
$R_9$ is H or OH; and
wherein $R_C$ is as defined above.

In some embodiments, Am is represented by formula (IA) or formula (IB),
wherein $R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH; and
wherein $R_C$ is as defined above.

In some embodiments, Am is represented by formula (IA) or formula (IB),
wherein $R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH; and
wherein $R_C$ is as defined above.

In some embodiments, Am is represented by formula (IA) or formula (IB),
wherein $R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH; and
wherein $R_C$ is as defined above.

In some embodiments, Am is represented by formula (II)

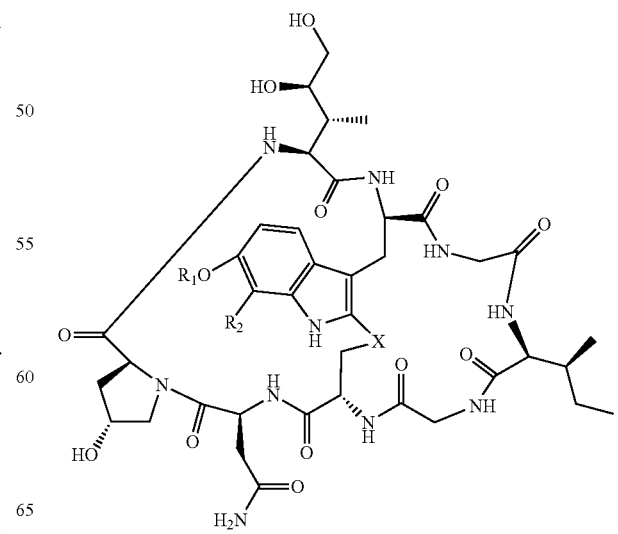

(II)

wherein X is S, SO, or SO$_2$; R$_1$ is H or a linker covalently bound to the antibody or antigen-binding fragment thereof; and R$_2$ is H or a linker covalently bound to the antibody or antigen-binding fragment thereof; wherein when R$_1$ is H, R$_2$ is the linker, and when R$_2$ is H, R$_1$ is the linker.

In some embodiments of any of the above aspects, the cytotoxin is a maytansinoid selected from the group consisting of DM1 and DM4. In some embodiments, the cytotoxin is an auristatin selected from the group consisting of monomethyl auristatin E and monomethyl auristatin F. In some embodiments, the cytotoxin is an anthracycline selected from the group consisting of daunorubicin, doxorubicin, epirubicin, and idarubicin.

In another aspect, the invention features a method of depleting a population of CD117+ cells in a human patient by administering an effective amount of an antibody or antigen-binding fragment thereof capable of binding GNNK+CD117.

In an additional, the invention features a method of depleting a population of CD117+ cells in a human patient in need of a hematopoietic stem cell transplant by administering, prior to the patient receiving a transplant containing hematopoietic stem cells, an effective amount of an antibody or antigen-binding fragment thereof capable of binding GNNK+CD117.

In another aspect, the invention features a method, for example, of treating a human patient in need of a hematopoietic stem cell transplant, including administering to a human patient a transplant containing hematopoietic stem cells, wherein the patient has been previously administered an antibody or antigen-binding fragment thereof capable of binding GNNK+CD117 in an amount sufficient to deplete a population of CD117+ cells in the patient.

In an additional aspect, the invention features a method, for example, of treating a human patient in need of a hematopoietic stem cell transplant, including: administering to a human patient an antibody or antigen-binding fragment thereof capable of binding GNNK+CD117 in an amount sufficient to deplete a population of CD117+ cells in the patient, and subsequently administering to the patient a transplant including hematopoietic stem cells.

In some embodiments of any of the above aspects, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In some embodiments of any of the above aspects, the antibody, antigen-binding fragment thereof, or ligand is internalized by a hematopoietic cell, such as a hematopoietic stem cell, cancer cell, or autoimmune cell following administration to the patient. For instance, the antibody, antigen-binding fragment thereof, or ligand may be internalized by hematopoietic stem cells, cancer cells, or autoimmune cells by receptor-mediated endocytosis (e.g., upon binding to cell-surface CD117, such as GNNK+CD117). In some embodiments, a cytotoxin covalently bound to the antibody or antigen-binding fragment thereof may be released intracellularly by chemical cleavage (for instance, by enzymatic or non-specific cleavage of a linker described herein). The cytotoxin may then access its intracellular target (such as the mitotic spindle apparatus, nuclear DNA, ribosomal RNA, or topoisomerases, among others) so as to promote the death of an endogenous hematopoietic cell, such as an endogenous hematopoietic stem cell prior to transplantation therapy, an endogenous cancer cell, or an endogenous autoimmune cell, among others.

In some embodiments of any of the above aspects, the antibody, antigen-binding fragment thereof, or ligand is capable of promoting necrosis of a hematopoietic cell, such as a hematopoietic stem cell, cancer cell, or autoimmune cell, among others. In some embodiments, the antibody or antigen-binding fragment thereof may promote the death of an endogenous hematopoietic stem cell prior to transplantation therapy, an endogenous cancer cell, or an endogenous autoimmune cell, among others, by recruiting one or more complement proteins, natural killer (NK) cells, macrophages, neutrophils, and/or eosinophils to the cell, such as a hematopoietic stem cell upon administration to the patient.

In some embodiments of any of the above aspects, the transplant containing hematopoietic stem cells is administered to the patient after the concentration of the antibody or antigen-binding fragment thereof has substantially cleared from the blood of the patient.

In some embodiments of any of the above aspects, the hematopoietic stem cells or progeny thereof maintain hematopoietic stem cell functional potential after two or more days (for example, from about 2 to about 5 days, from about 2 to about 7 days, from about 2 to about 20 days, from about 2 to about 30 days, such as 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 22 days, 23 days, 24 days, 25 days, 26 days, 27 days, 28 days, 29 days, 30 days, or more) following transplantation of the hematopoietic stem cells into the patient.

In some embodiments of any of the above aspects, the hematopoietic stem cells or progeny thereof are capable of localizing to hematopoietic tissue, such as the bone marrow, and/or reestablishing hematopoiesis following transplantation of the hematopoietic stem cells into the patient.

In some embodiments of any of the above aspects, upon transplantation into the patient, the hematopoietic stem cells give rise to recovery of a population of cells selected from the group consisting of megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes.

In some embodiments of any of the above aspects, the method is used to treat one or more disorders, such as by depleting a population of hematopoietic stem cells in a patient prior to hematopoietic stem cell transplant therapy so as to provide a niche to which the transplanted hematopoietic stem cells may home. Following transplantation, the hematopoietic stem cells may establish productive hematopoiesis, so as to replenish a deficient cell type in the patient or a cell type that is being actively killed or has been killed, for instance, by chemotherapeutic methods. For instance, the patient may be one that is suffering from a stem cell disorder. In some embodiments, the patient is suffering from a hemoglobinopathy disorder, such as sickle cell anemia, thalassemia, Fanconi anemia, aplastic anemia, and Wiskott-Aldrich syndrome. The patient may be suffering from an immunodeficiency disorder, such as a congenital immunodeficiency disorder or an acquired immunodeficiency disorder (e.g., human immunodeficiency virus or acquired immune deficiency syndrome). In some embodiments, the patient is suffering from a metabolic disorder, such as glycogen storage diseases, mucopolysaccharidoses, Gaucher's Disease, Hurlers Disease, sphingolipidoses, and metachromatic leukodystrophy. In some embodiments, the patient is suffering from a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis. In some embodiments, the patient is suffering from an autoimmune disease, such as scleroderma, multiple sclerosis, ulcerative colitis, Chron's disease, ant Type 1 diabetes. In some embodiments, the patient is suffering from cancer or myeloproliferative disease, such as a hematological cancer. In some embodiments, the patient is suffering from acute myeloid leukemia, acute lymphoid leukemia, chronic myeloid leukemia, chronic lymohoid leukemia, multiple meloma, diffuse large B-cell lymphoma, or non-Hodgkin's lymphoma. In some embodiments, the patient is suffering from a myelodysplastic disease, such as myelodysplastic syndrome.

In some embodiments of any of the above aspects, the method is used to directly treat a cancer, such as a cancer characterized by CD117+ cells (e.g., a leukemia characterized by CD117+ cells), by administration of an antibody, antigen-binding fragment thereof, or ligand that depletes a population of CD117+ cancer cells in the patient and/or by administration of an antibody, antigen-binding fragment thereof, or ligand so as to deplete a population of endogenous hematopoietic stem cells prior to hematopoietic stem cell transplantation. In the latter case, the transplantation may in turn re-constitute, for example, a population of cells depleted during the process of eradicating cancer cells. The cancer may be a hematological cancer, such as acute myeloid leukemia, acute lymphoid leukemia, chronic myeloid leukemia, chronic lymohoid leukemia, multiple meloma, diffuse large B-cell lymphoma, or non-Hodgkin's lymphoma.

In some embodiments of any of the above aspects, the method is used to treat an autoimmune disease, such as by administration of an antibody, antigen-binding fragment thereof, or ligand so as to deplete a population of CD117+ autoimmune cells and/or by administration of an antibody, antigen-binding fragment thereof, or ligand so as to deplete a population of endogenous hematopoietic stem cells prior to hematopoietic stem cell transplantation. In the latter case, the transplantation may in turn re-constitute, for example, a population of cells depleted during the process of eradicating autoimmune cells. The autoimmune disease may be, for example, scleroderma, multiple sclerosis (MS), human systemic lupus (SLE), rheumatoid arthritis (RA), inflammatory bowel disease (IBD), treating psoriasis, Type 1 diabetes mellitus (Type 1 diabetes), acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis.

Thus, in some embodiments of any of the above aspects, the invention features a method of treating a hemoglobinopathy disorder, such as sickle cell anemia, thalassemia, Fanconi anemia, aplastic anemia, and Wiskott-Aldrich syndrome. In some embodiments, the invention features a method of treating an immunodeficiency disorder, such as a congenital immunodeficiency disorder or an acquired immunodeficiency disorder (e.g., human immunodeficiency virus or acquired immune deficiency syndrome). In some embodiments, the invention features a method of treating a metabolic disorder, such as glycogen storage diseases, mucopolysaccharidoses, Gaucher's Disease, Hurlers Disease, sphingolipidoses, and metachromatic leukodystrophy. In some embodiments, the invention features a method of treating a disorder selected from the group consisting of adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, and juvenile rheumatoid arthritis In some embodiments, the invention features a method of treating an autoimmune disease, such as scleroderma, multiple sclerosis, ulcerative colitis, Chron's disease, ant Type 1 diabetes. In some embodiments, the invention features a method of treating a cancer or myeloproliferative disease, such as a hematological cancer. In some embodiments, the invention features a method of treating acute myeloid leukemia, acute lymphoid leukemia, chronic myeloid leukemia, chronic lymohoid leukemia, multiple meloma, diffuse large B-cell lymphoma, or non-Hodgkin's lymphoma. In some embodiments, the patient is suffering from a myelodyplastic disease, such as myelodysplastic syndrome. In these embodiments, the method may include the steps of administering an antibody, antigen-binding fragment thereof, or ligand that binds CD117 (e.g., GNNK+CD117) and/or a hematopoietic stem cell transplant according to the method of any of the above-described aspects and embodiments of the invention.

Similarly, in some embodiments of any of the above aspects, the invention provides a method of treating cancer directly, such as a cancer characterized by CD117+ cells (e.g., a leukemia characterized by CD117+ cells). In these embodiments, the method includes administering an antibody, antigen-binding fragment thereof, or ligand that binds CD117 (e.g., GNNK+CD117). The cancer may be a hematological cancer, such as acute myeloid leukemia, acute lymphoid leukemia, chronic myeloid leukemia, chronic lymohoid leukemia, multiple meloma, diffuse large B-cell lymphoma, or non-Hodgkin's lymphoma.

Additionally, in some embodiments of any of the above aspects, the invention provides a method of treating an autoimmune disease, such as multiple sclerosis (MS), human systemic lupus (SLE), rheumatoid arthritis (RA), inflammatory bowel disease (IBD), treating psoriasis, Type 1 diabetes mellitus (Type 1 diabetes) acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, uveitis, vasculitis, vitiligo, vulvodynia ("vulvar vestibulitis"), and Wegener's granulomatosis. In these embodiments, the method includes administering an antibody, antigen-binding fragment thereof, or ligand that binds CD117 (e.g., GNNK+CD117).

In another aspect, the invention features a method of depleting a population of CD117+(e.g., GNNK+CD117+) cells by contacting the population with an effective amount of a conjugate represented by the formula Ab-Am, wherein Ab is an antibody or antigen-binding fragment thereof that binds CD117 and Am is an amatoxin. Am may be represented by formula (IA)

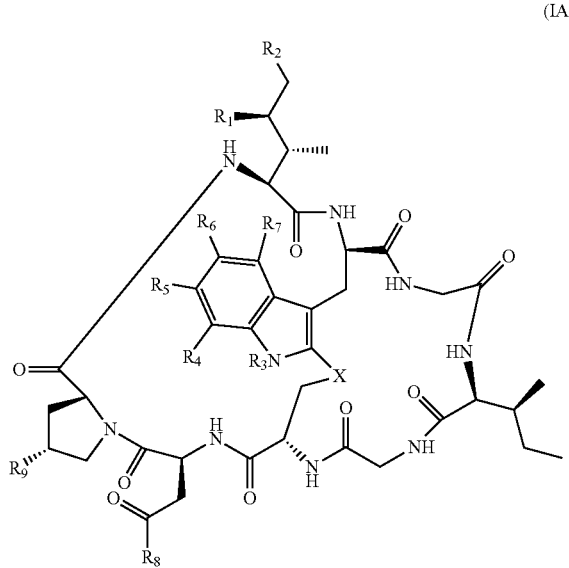

(IA)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocyclolalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene; and
Z is a chemical moiety formed from a coupling reaction between a reactive substituent present on L and a reactive substituent present within the antibody or antigen-binding fragment thereof,
wherein Am contains exactly one $R_C$ substituent.

In some embodiments, Am is represented by formula (IB)

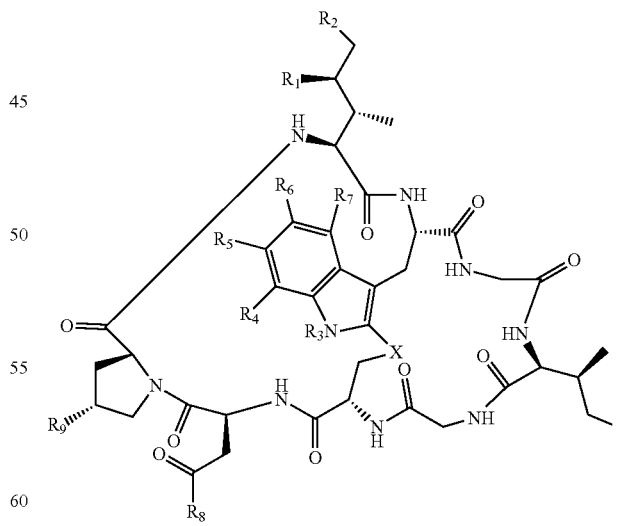

(IB)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocyclolalkyl group;

$R_3$ is H, $R_C$, or $R_D$;

$R_4$ is H, OH, $OR_C$, $OR_D$, $R_C$, or $R_D$;

$R_5$ is H, OH, $OR_C$, $OR_D$, $R_C$, or $R_D$;

$R_6$ is H, OH, $OR_C$, $OR_D$, $R_C$, or $R_D$;

$R_7$ is H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene;

Z is a chemical moiety formed from a coupling reaction between a reactive substituent present on L and a reactive substituent present within an antibody, antigen-binding fragment thereof, or ligand that binds CD117 (such as GNNK+ CD117); and wherein Am contains exactly one $R_C$ substituent.

In another aspect, the invention features a conjugate represented by the formula Ab-Am, wherein Ab is an antibody or antigen-binding fragment thereof that binds CD117 (e.g., GNNK+CD117) and Am is an amatoxin. In some embodiments, Am is represented by formula (IA) or formula (IB), above.

In some embodiments of the preceding two aspects, the antibody or antigen-binding fragment thereof is conjugated to the amatoxin by way of a cysteine residue in the Fc domain of the antibody or antigen-binding fragment thereof. In some embodiments, the cysteine residue is introduced by way of a mutation in the Fc domain of the antibody or antigen-binding fragment thereof. For instance, the cysteine residue may be selected from the group consisting of Cys118, Cys239, and Cys265.

In some embodiments of these aspects, the cysteine residue is naturally occurring in the Fc domain of the antibody or antigen-binding fragment thereof. For instance, the Fc domain may be an IgG Fc domain, such as a human IgG1 Fc domain, and the cysteine residue may be selected from the group consisting of Cys261, Csy321, Cys367, and Cys425.

In some embodiments of these aspects, $R_1$ is H, OH, or $OR_A$;

$R_2$ is H, OH, or $OR_B$;

$R_A$ and $R_B$, together with the oxygen atoms to which they are bound, combine to form:

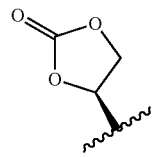 [SMILES: *[C@@H]1COC(=O)O1]

$R_3$, $R_4$, $R_6$, and $R_7$ are each H;

$R_5$ is $OR_C$;

$R_8$ is OH or $NH_2$; and $R_9$ is H or OH.

In some embodiments, $R_1$ and $R_2$ are each independently H or OH;

$R_3$ is $R_C$;

$R_4$, $R_6$, and $R_7$ are each H;

$R_5$ is H, OH, or $OC_1$-$C_6$ alkyl;

$R_8$ is OH or $NH_2$; and $R_9$ is H or OH.

In some embodiments, $R_1$ and $R_2$ are each independently H or OH;

$R_3$, $R_6$, and $R_7$ are each H;

$R_4$ is $OR_C$, or $R_C$;

$R_5$ is H, OH, or $OC_1$-$C_6$ alkyl;

$R_8$ is OH or $NH_2$; and $R_9$ is H or OH.

In some embodiments, $R_1$ and $R_2$ are each independently H or OH;

$R_3$, $R_6$, and $R_7$ are each H;

$R_4$ and $R_5$ are each independently H or OH;

$R_8$ is $OR_C$ or $NHR_C$; and $R_9$ is H or OH.

In some embodiments of these aspects, the antibody or antigen-binding fragment thereof is internalized by a CD117+ cell.

In some embodiments of these aspects, the antibody or antigen-binding fragment thereof binds CD117 with a $K_d$ of less than 1 µM, less than 750 nM, less than 500 nM, less than 250 nM, less than 200 nM, less than 150 nM, less than 100 nM, less than 75 nM, less than 50 nM, less than 10 nM, less than 1 nM, less than 0.1 nM, less than 10 pM, less than 1 pM, or less than 0.1 pM. In some embodiments, the $K_d$ is from about 0.1 pM to about 1 µM.

In some embodiments of these aspects, the antibody or antigen-binding fragment thereof binds CD117 with a $k_{on}$ of from about $9 \times 10^{-2}$ $M^{-1}$ $s^{-1}$ to about $1 \times 10^2$ $M^{-1}$ $s^{-1}$.

In some embodiments of these aspects, the antibody or antigen-binding fragment thereof competitively inhibits the binding of CD117 to a second antibody or antigen binding fragment thereof, wherein the second antibody or antigen-binding fragment thereof has the following complementarity determining regions (CDRs):

a. a CDR-H1 having the amino acid sequence SYWIG (SEQ ID NO: 1);

b. a CDR-H2 having the amino acid sequence IIYPGDS-DTRYSPSFQG (SEQ ID NO: 2);

c. a CDR-H3 having the amino acid sequence HGRGYN-GYEGAFDI (SEQ ID NO: 3);

d. a CDR-L1 having the amino acid sequence RASQGIS-SALA (SEQ ID NO: 4);

e. a CDR-L2 having the amino acid sequence DASSLES (SEQ ID NO: 5); and f. a CDR-L3 having the amino acid sequence CQQFN-SYPLT (SEQ ID NO: 6).

In some embodiments of these aspects, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFV.

In another aspect, the invention features a conjugate represented by the formula Ab-Cy, wherein Ab is an antibody or antigen-binding fragment thereof that binds CD117 (e.g., GNNK+CD117) and Cy is a cytotoxin. In some embodiments of this aspect, the cytotoxin is pseudomonas exotoxin A, deBouganin, diphtheria toxin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, or an indolinobenzodiazepine dimer, or a variant of any of the foregoing cytotoxins.

In some embodiments of this aspect, the antibody or antigen-binding fragment thereof is internalized by a CD117+ cell.

In some embodiments of this aspect, the antibody or antigen-binding fragment thereof binds CD117 with a $K_d$ of less than 1 µM, less than 750 nM, less than 500 nM, less than 250 nM, less than 200 nM, less than 150 nM, less than 100 nM, less than 75 nM, less than 50 nM, less than 10 nM, less than 1 nM, less than 0.1 nM, less than 10 pM, less than 1 pM, or less than 0.1 pM. In some embodiments, the $K_d$ is from about 0.1 pM to about 1 µM.

In some embodiments of this aspect, the antibody or antigen-binding fragment thereof binds CD117 with a $k_{on}$ of from about $9 \times 10^{-2}$ $M^{-1}$ $s^{-1}$ to about $1 \times 10^2$ $M^{-1}$ $s^{-1}$.

In some embodiments of this aspect, the antibody or antigen-binding fragment thereof competitively inhibits the binding of CD117 to a second antibody or antigen binding fragment thereof, wherein the second antibody or antigen-binding fragment thereof has the following CDRs:
 a. a CDR-H1 having the amino acid sequence SYWIG (SEQ ID NO: 1);
 b. a CDR-H2 having the amino acid sequence IIYPGDS-DTRYSPSFQG (SEQ ID NO: 2);
 c. a CDR-H3 having the amino acid sequence HGRGYN-GYEGAFDI (SEQ ID NO: 3);
 d. a CDR-L1 having the amino acid sequence RASQGIS-SALA (SEQ ID NO: 4);
 e. a CDR-L2 having the amino acid sequence DASSLES (SEQ ID NO: 5); and
 f. a CDR-L3 having the amino acid sequence CQQFN-SYPLT (SEQ ID NO: 6).

In some embodiments of this aspect, the antibody or antigen-binding fragment thereof is selected from the group consisting of a monoclonal antibody or antigen-binding fragment thereof, a polyclonal antibody or antigen-binding fragment thereof, a humanized antibody or antigen-binding fragment thereof, a bispecific antibody or antigen-binding fragment thereof, a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv. In some embodiments, the antibody has an isotype selected from the group consisting of IgG, IgA, IgM, IgD, and IgE.

In another aspect, the invention features a ligand or fragment thereof that binds CD117 (e.g., GNNK+CD117) covalently bound to an Fc domain, such as a dimeric Fc domain isolated from a human antibody (for example, isolated from an IgG1, IgG2, IgG3, or IgG4 isotype human antibody). In some embodiments of this aspect, the Fc domain is a monomeric Fc domain containing a single polypeptide strand. In some embodiments of this aspect, the N-terminus of the ligand or fragment thereof is bound to the Fc domain. In some embodiments of this aspect, the C-terminus of the ligand or fragment thereof is bound to the Fc domain. The Fc domain may be conjugated to one or more copies of the ligand or fragment thereof. For instance, conjugates described herein include dimeric Fc domains in which each polypeptide strand of the Fc domain is conjugated to the ligand or fragment thereof. The Fc domain may in turn be conjugated to a cytotoxin, such as a cytotoxin described herein (for example, pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof).

In some embodiments of this aspect, the ligand or fragment thereof is covalently bound to a cytotoxin, such as a cytotoxin described herein (for example, pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof). In some embodiments of this aspect, the N-terminus of the ligand or fragment thereof is bound to the cytotoxin. In some embodiments of this aspect, the C-terminus of the ligand or fragment thereof is bound to the cytotoxin. The cytotoxin may in turn be conjugated to an Fc domain.

In some embodiments of this aspect, the ligand or fragment thereof is covalently bound to the cytotoxin at one site on the ligand or fragment thereof (for example, the N- or C-terminus of the ligand or fragment thereof) and is covalently bound to an Fc domain at another site on the ligand or fragment thereof (for example, the opposite terminus of the ligand or fragment thereof).

In some embodiments of this aspect, the Fc domain is a human IgG1 isotype Fc domain. In some embodiments of this aspect, the Fc domain is a human IgG2 isotype Fc domain. In some embodiments of this aspect, the Fc domain is a human IgG3 isotype Fc domain. In some embodiments of this aspect, the Fc domain is a human IgG4 isotype Fc domain.

DETAILED DESCRIPTION

Figure 1:
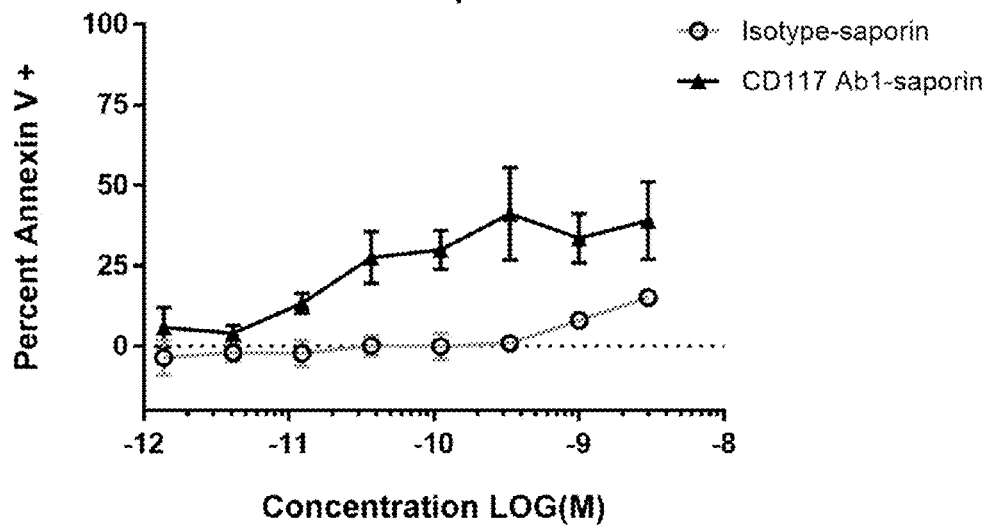
FIG. 1 is a graph demonstrating the effect of various concentrations of anti-CD117 monoclonal antibody or isotype-matched negative control, each conjugated to saporin by way of saporin-conjugated Fab fragments, on the viability of Kasumi-1 cells in vitro. Cell viability was assessed by Annexin V staining as described in Example 4, below.

The invention provides methods of treating a variety of disorders, such as diseases of a cell type in the hematopoietic lineage, cancers, autoimmune diseases, metabolic disorders, and stem cell disorders, among others. The compositions and methods described herein may (i) directly deplete a population of cells that give rise to a pathology, such as a population of cancer cells (e.g., leukemia cells) and autoimmune cells (e.g., autoreactive T-cells), and/or (ii) deplete a population of endogenous hematopoietic stem cells so as to promote the engraftment of transplanted hematopoietic stem cells by providing a niche to which the transplanted cells may home. The foregoing activities can be achieved by administration of an antibody, antigen-binding fragment thereof, or ligand capable of binding an antigen expressed by an endogenous disease-causing cell or a hematopoietic stem cell. In the case of direct treatment of a disease, this administration can cause a reduction in the quantity of the cells that give rise to the pathology of interest. In the case of preparing a patient for hematopoietic stem cell transplant therapy, this administration can cause the selective depletion of a population of endogenous hematopoietic stem cells, thereby creating a vacancy in the hematopoietic tissue, such as the bone marrow, that can subsequently be filled by transplanted, exogenous hematopoietic stem cells. The invention is based in part on the discovery that antibodies, antigen-binding fragments thereof, and ligands capable of binding CD117 (such as GNNK+D117) can be administered to a patient to effect both of the above activities. Antibodies, antigen-binding fragments thereof, and ligands that bind CD117 can be administered to a patient suffering from a cancer or autoimmune disease to directly deplete a population of cancerous cells or autoimmune cells, and can also be administered to a patient in need of hematopoietic stem cell transplant therapy in order to promote the survival and engraftment potential of transplanted hematopoietic stem cells.

Engraftment of hematopoietic stem cell transplants due to the administration of anti-CD117 antibodies, antigen-binding fragments thereof, or ligands can manifest in a variety of empirical measurements. For instance, engraftment of transplanted hematopoietic stem cells can be evaluated by assessing the quantity of competitive repopulating units (CRU) present within the bone marrow of a patient following administration of an antibody or antigen-binding fragment thereof capable of binding CD117 and subsequent administration of a hematopoietic stem cell transplant. Additionally, one can observe engraftment of a hematopoietic stem cell transplant by incorporating a reporter gene, such as an enzyme that catalyzes a chemical reaction yielding a fluorescent, chromophoric, or luminescent product, into a vector with which the donor hematopoietic stem cells have been transfected and subsequently monitoring the corresponding signal in a tissue into which the hematopoietic stem cells have homed, such as the bone marrow. One can also observe hematopoietic stem cell engraftment by evaluation of the quantity and survival of hematopoietic stem and progenitor cells, for instance, as determined by fluorescence activated cell sorting (FACS) analysis methods known in the art. Engraftment can also be determined by measuring white blood cell counts in peripheral blood during a post-transplant period, and/or by measuring recovery of marrow cells by donor cells in a bone marrow aspirate sample.

The sections that follow provide a description of antibodies, antigen-binding fragments thereof, and ligands that can be administered to a patient, such as a patient suffering from a cancer or autoimmune disease, or a patient in need of hematopoietic stem cell transplant therapy in order to promote engraftment of hematopoietic stem cell grafts, as well as methods of administering such therapeutics to a patient (e.g., prior to hematopoietic stem cell transplantation).

Definitions

As used herein, the term "about" refers to a value that is within 10% above or below the value being described. For example, the term "about 5 nM" indicates a range of from 4.5 nM to 5.5 nM.

As used herein, the term "amatoxin" refers to a member of the amatoxin family of peptides produced by *Amanita phalloides* mushrooms, or a variant or derivative thereof, such as a variant or derivative thereof capable of inhibiting RNA polymerase II activity. Amatoxins useful in conjunction with the compositions and methods described herein include compounds according to formula (III), below, such as α-amanitin, β-amanitin, γ-amanitin, ε-amanitin, amanin, amaninamide, amanullin, amanullinic acid, and proamanullin. Formula (III) is as follows:

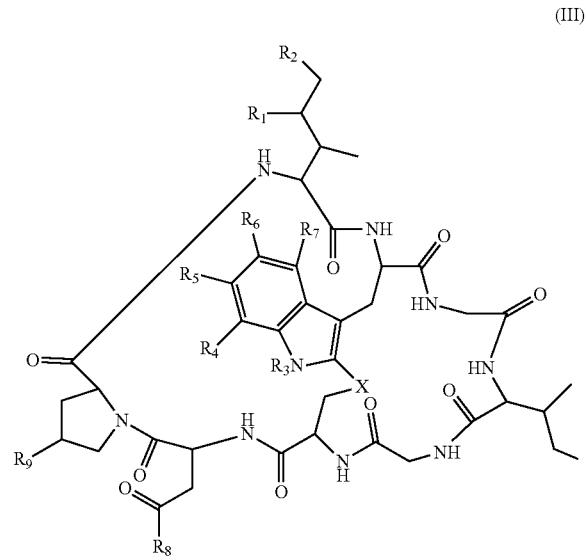

(III)

wherein $R_1$ is H, OH, or $OR_A$;

$R_2$ is H, OH, or $OR_B$;

$R_A$ and $R_B$, together with the oxygen atoms to which they are bound, combine to form an optionally substituted 5-membered heterocyclolalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —SO$_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

For instance, amatoxins useful in conjunction with the compositions and methods described herein include compounds according to formula (IIIA), below:

(IIIA)

wherein $R_1$ is H, OH, or $OR_A$;

$R_2$ is H, OH, or $OR_B$;

$R_A$ and $R_B$, together with the oxygen atoms to which they are bound, combine to form an optionally substituted 5-membered heterocyclolalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, or $R_D$;

$R_8$ is OH, $NH_2$, or $OR_D$;

$R_9$ is H, OH, or $OR_D$;

X is —S—, —S(O)—, or —SO$_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

Amatoxins useful in conjunction with the compositions and methods described herein also include compounds according to formula (IIIB), below:

(IIIB)

wherein $R_1$ is H, OH, or $OR_A$;

$R_2$ is H, OH, or $OR_B$;

$R_A$ and $R_B$, together with the oxygen atoms to which they are bound, combine to form an optionally substituted 5-membered heterocyclolalkyl group;

$R_3$ is H or $R_D$;

$R_4$ is H, OH, $OR_D$, or $R_D$;

$R_5$ is H, OH, $OR_D$, or $R_D$;

$R_6$ is H, OH, $OR_D$, or $R_D$;

$R_7$ is H, OH, $OR_D$, Or $R_D$;

$R_8$ is OH, $NH_2$, or $OR_D$;

$R_9$ is H, OH, or $OR_D$;

X is —S—, —S(O)—, or —SO$_2$—; and $R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl.

As described herein, amatoxins may be conjugated to an antibody, antigen-binding fragment thereof, or ligand, for instance, by way of a linker moiety. Exemplary methods of amatoxin conjugation and linkers useful for such processes are described in the section entitled "Linkers for chemical conjugation," as well as in Table 1, below. Exemplary linker-containing amatoxins useful for conjugation to an antibody, antigen-binding fragment, or ligand in accordance with the compositions and methods described herein are shown in structural formulas (I), (IA), (IB), and (II), recited herein.

As used herein, the term "antibody" refers to an immunoglobulin molecule that specifically binds to, or is immunologically reactive with, a particular antigen, and includes polyclonal, monoclonal, genetically engineered, and otherwise modified forms of antibodies, including but not limited to chimeric antibodies, humanized antibodies, heteroconjugate antibodies (e.g., bi- tri- and quad-specific antibodies, diabodies, triabodies, and tetrabodies), and antigen binding fragments of antibodies, including, for example, Fab', F(ab')$_2$, Fab, Fv, rIgG, and scFv fragments. Unless otherwise indicated, the term "monoclonal antibody" (mAb) is meant to include both intact molecules, as well as antibody fragments (including, for example, Fab and F(ab')$_2$ fragments) that are capable of specifically binding to a target protein. As used herein, the Fab and F(ab')$_2$ fragments refer to antibody fragments that lack the Fc fragment of an intact antibody. Examples of these antibody fragments are described herein.

The term "antigen-binding fragment," as used herein, refers to one or more fragments of an antibody that retain the ability to specifically bind to a target antigen. The antigen-binding function of an antibody can be performed by fragments of a full-length antibody. The antibody fragments can be, for example, a Fab, F(ab')$_2$, scFv, diabody, a triabody, an affibody, a nanobody, an aptamer, or a domain antibody. Examples of binding fragments encompassed of the term "antigen-binding fragment" of an antibody include, but are not limited to: (i) a Fab fragment, a monovalent fragment consisting of the $V_L$, $V_H$, $C_L$, and $C_H1$ domains; (ii) a F(ab')$_2$ fragment, a bivalent fragment containing two Fab fragments linked by a disulfide bridge at the hinge region; (iii) a Fd fragment consisting of the $V_H$ and $C_H1$ domains; (iv) a Fv fragment consisting of the $V_L$ and $V_H$ domains of a single arm of an antibody, (v) a dAb including $V_H$ and $V_L$ domains; (vi) a dAb fragment that consists of a $V_H$ domain (see, e.g., Ward et al., Nature 341:544-546, 1989); (vii) a dAb which consists of a $V_H$ or a $V_L$ domain; (viii) an isolated complementarity determining region (CDR); and (ix) a combination of two or more (e.g., two, three, four, five, or six) isolated CDRs which may optionally be joined by a synthetic linker. Furthermore, although the two domains of the Fv fragment, $V_L$ and $V_H$, are coded for by separate genes, they can be joined, using recombinant methods, by a linker that enables them to be made as a single protein chain in which the $V_L$ and $V_H$ regions pair to form monovalent molecules (known as single chain Fv (scFv); see, for example, Bird et al., Science 242:423-426, 1988 and Huston et al., Proc. Natl. Acad. Sci. USA 85:5879-5883, 1988). These antibody fragments can be obtained using conventional techniques known to those of skill in the art, and the fragments can be screened for utility in the same manner as intact antibodies. Antigen-binding fragments can be produced by recombinant DNA techniques, enzymatic or chemical cleavage of intact immunoglobulins, or, in certain cases, by chemical peptide synthesis procedures known in the art.

As used herein, the term "anti-CD117 antibody" refers to a protein or peptide-containing molecule that includes at least a portion of an immunoglobulin molecule, such as but not limited to at least one complementarity determining region (CDR) of a heavy or light chain or a ligand binding portion thereof, a heavy chain or light chain variable region, a heavy chain or light chain constant region, a framework region, or any portion thereof, that is capable of specifically binding to CD117 (for example, GNNK+CD117). Anti-CD117 antibodies also include antibody-like protein scaffolds, such as the tenth fibronectin type III domain ($^{10}$Fn3), which contains BC, DE, and FG structural loops similar in structure and solvent accessibility to antibody CDRs. The tertiary structure of the $^{10}$Fn3 domain resembles that of the variable region of the IgG heavy chain, and one of skill in the art can graft, for example, the CDRs of an anti-CD117 monoclonal antibody onto the fibronectin scaffold by replacing residues of the BC, DE, and FG loops of $^{10}$Fn3 with residues from the CDRH-1, CDRH-2, or CDRH-3 regions of an anti-CD117 monoclonal antibody.

As used herein, the term "bispecific antibody" refers to, for example, a monoclonal, often a human or humanized antibody that is capable of binding at least two different antigens. For instance, one of the binding specificities can be directed towards a hematopoietic stem cell surface antigen, CD117 (e.g., GNNK+CD117), and the other can specifically bind a different hematopoietic stem cell surface antigen or another cell surface protein, such as a receptor or receptor subunit involved in a signal transduction pathway that potentiates cell growth, among others.

As used herein, the term "complementarity determining region" (CDR) refers to a hypervariable region found both in the light chain and the heavy chain variable domains of an antibody. The more highly conserved portions of variable domains are referred to as framework regions (FRs). The amino acid positions that delineate a hypervariable region of an antibody can vary, depending on the context and the various definitions known in the art. Some positions within a variable domain may be viewed as hybrid hypervariable positions in that these positions can be deemed to be within a hypervariable region under one set of criteria while being deemed to be outside a hypervariable region under a different set of criteria. One or more of these positions can also be found in extended hypervariable regions. The antibodies described herein may contain modifications in these hybrid hypervariable positions. The variable domains of native heavy and light chains each contain four framework regions that primarily adopt a β-sheet configuration, connected by three CDRs, which form loops that connect, and in some cases form part of, the β-sheet structure. The CDRs in each chain are held together in close proximity by the framework regions in the order FR1-CDR1-FR2-CDR2-FR3-CDR3-FR4 and, with the CDRs from the other antibody chains, contribute to the formation of the target binding site of antibodies (see Kabat et al., Sequences of Proteins of Immunological Interest, National Institute of Health, Bethesda, Md., 1987). As used herein, numbering of immunoglobulin amino acid residues is performed according to the immunoglobulin amino acid residue numbering system of Kabat et al., unless otherwise indicated.

As used herein, the terms "condition" and "conditioning" refer to processes by which a patient is prepared for receipt of a transplant containing hematopoietic stem cells. Such procedures promote the engraftment of a hematopoietic stem cell transplant (for instance, as inferred from a sustained increase in the quantity of viable hematopoietic stem cells within a blood sample isolated from a patient following a conditioning procedure and subsequent hematopoietic stem cell transplantation. According to the methods described herein, a patient may be conditioned for hematopoietic stem cell transplant therapy by administration to the patient of an antibody or antigen-binding fragment thereof capable of binding an antigen expressed by hematopoietic stem cells, such as CD117 (e.g., GNNK+CD117). As described herein, the antibody may be covalently conjugated to a cytotoxin so as to form a drug-antibody conjugate. Administration of an antibody, antigen-binding fragment thereof, or drug-antibody conjugate capable of binding one or more of the foregoing antigens to a patient in need of hematopoietic stem cell transplant therapy can promote the engraftment of a hematopoietic stem cell graft, for example, by selectively depleting endogenous hematopoietic stem cells, thereby creating a vacancy filled by an exogenous hematopoietic stem cell transplant.

As used herein, the term "conjugate" refers to a compound formed by the chemical bonding of a reactive functional group of one molecule, such as an antibody or antigen-binding fragment thereof, with an appropriately reactive functional group of another molecule, such as a cytotoxin described herein. Conjugates may include a linker between the two molecules bound to one another. Examples of linkers that can be used for the formation of a conjugate include peptide-containing linkers, such as those that contain naturally occurring or non-naturally occurring amino acids, such as D-amino acids. Linkers can be prepared using a variety of strategies described herein and known in the art. Depending on the reactive components therein, a linker may be cleaved, for example, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012).

As used herein, the term "coupling reaction" refers to a chemical reaction in which two or more substituents suitable for reaction with one another react so as to form a chemical moiety that joins (e.g., covalently) the molecular fragments bound to each substituent. Coupling reactions include those in which a reactive substituent bound to a fragment that is a cytotoxin, such as a cytotoxin known in the art or described herein, reacts with a suitably reactive substituent bound to a fragment that is an antibody, antigen-binding fragment thereof, or ligand, such as an antibody, antigen-binding fragment thereof, or ligand specific for CD117 (such as GNNK+CD117) known in the art or described herein. Examples of suitably reactive substituents include a nucleophile/electrophile pair (e.g., a thiol/haloalkyl pair, an amine/carbonyl pair, or a thiol/$\alpha,\beta$-unsaturated carbonyl pair, among others), a diene/dienophile pair (e.g., an azide/alkyne pair, among others), and the like. Coupling reactions include, without limitation, thiol alkylation, hydroxyl alkylation, amine alkylation, amine condensation, amidation, esterification, disulfide formation, cycloaddition (e.g., [4+2] Diels-Alder cycloaddition, [3+2] Huisgen cycloaddition, among others), nucleophilic aromatic substitution, electrophilic aromatic substitution, and other reactive modalities known in the art or described herein.

As used herein, "CRU (competitive repopulating unit)" refers to a unit of measure of long-term engrafting stem cells, which can be detected after in-vivo transplantation.

As used herein, the term "donor" refers to a human or animal from which one or more cells are isolated prior to administration of the cells, or progeny thereof, into a recipient. The one or more cells may be, for example, a population of hematopoietic stem cells.

As used herein, the term "diabody" refers to a bivalent antibody containing two polypeptide chains, in which each polypeptide chain includes $V_H$ and $V_L$ domains joined by a linker that is too short (e.g., a linker composed of five amino acids) to allow for intramolecular association of $V_H$ and $V_L$ domains on the same peptide chain. This configuration forces each domain to pair with a complementary domain on another polypeptide chain so as to form a homodimeric structure. Accordingly, the term "triabody" refers to trivalent antibodies containing three peptide chains, each of which contains one $V_H$ domain and one $V_L$ domain joined by a linker that is exceedingly short (e.g., a linker composed of 1-2 amino acids) to permit intramolecular association of $V_H$ and $V_L$ domains within the same peptide chain. In order to fold into their native structures, peptides configured in this way typically trimerize so as to position the $V_H$ and $V_L$ domains of neighboring peptide chains spatially proximal to one another (see, for example, Holliger et al., Proc. Natl. Acad. Sci. USA 90:6444-48, 1993).

As used herein, a "dual variable domain immunoglobulin" ("DVD-Ig") refers to an antibody that combines the target-binding variable domains of two monoclonal antibodies via linkers to create a tetravalent, dual-targeting single agent (see, for example, Gu et al., Meth. Enzymol., 502:25-41, 2012).

As used herein, the term "endogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is found naturally in a particular organism, such as a human patient.

As used herein, the term "engraftment potential" is used to refer to the ability of hematopoietic stem and progenitor cells to repopulate a tissue, whether such cells are naturally circulating or are provided by transplantation. The term encompasses all events surrounding or leading up to engraftment, such as tissue homing of cells and colonization of cells within the tissue of interest. The engraftment efficiency or rate of engraftment can be evaluated or quantified using any clinically acceptable parameter as known to those of skill in the art and can include, for example, assessment of competitive repopulating units (CRU); incorporation or expression of a marker in tissue(s) into which stem cells have homed, colonized, or become engrafted; or by evaluation of the progress of a subject through disease progression, survival of hematopoietic stem and progenitor cells, or survival of a recipient. Engraftment can also be determined by measuring white blood cell counts in peripheral blood during a post-transplant period. Engraftment can also be assessed by measuring recovery of marrow cells by donor cells in a bone marrow aspirate sample.

As used herein, the term "exogenous" describes a substance, such as a molecule, cell, tissue, or organ (e.g., a hematopoietic stem cell or a cell of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte) that is not found naturally in a particular organism, such as a human patient. Exogenous substances include those that are provided from an external source to an organism or to cultured matter extracted therefrom.

As used herein, the term "framework region" or "FW region" includes amino acid residues that are adjacent to the CDRs of an antibody or antigen-binding fragment thereof. FW region residues may be present in, for example, human antibodies, humanized antibodies, monoclonal antibodies, antibody fragments, Fab fragments, single chain antibody fragments, scFv fragments, antibody domains, and bispecific antibodies, among others.

As used herein, the term "hematopoietic stem cells" ("HSCs") refers to immature blood cells having the capacity to self-renew and to differentiate into mature blood cells containing diverse lineages including but not limited to granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Such cells may include CD34+ cells. CD34+ cells are immature cells that express the CD34 cell surface marker. In humans, CD34+ cells are believed to include a subpopulation of cells with the stem cell properties defined above, whereas in mice, HSCs are CD34-. In addition, HSCs also refer to long term repopulating HSCs (LT-HSC) and short term repopulating HSCs (ST-HSC). LT-HSCs and ST-HSCs are differentiated, based on functional potential and on cell surface marker expression. For example, human HSCs are CD34+, CD38-, CD45RA-, CD90+, CD49F+, and lin- (negative for mature lineage markers including CD2, CD3, CD4, CD7, CD8, CD10, CD11B, CD19, CD20, CD56, CD235A). In mice, bone marrow LT-HSCs are CD34-, SCA-1+, C-kit+, CD135-, Slamfl/CD150+, CD48-, and lin- (negative for mature lineage markers including Ter119, CD11b, Gr1, CD3, CD4, CD8, B220, IL7ra), whereas ST-HSCs are CD34+, SCA-1+, C-kit+, CD135-, Slamfl/CD150+, and lin- (negative for mature lineage markers including Ter119, CD11b, Gr1, CD3, CD4, CD8, B220, IL7ra). In addition, ST-HSCs are less quiescent and more proliferative than LT-HSCs under homeostatic conditions. However, LT-HSC have greater self renewal potential (i.e., they survive throughout adulthood, and can be serially transplanted through successive recipients), whereas ST-HSCs have limited self renewal (i.e., they survive for only a limited period of time, and do not possess serial transplantation potential). Any of these HSCs can be used in the methods described herein. ST-HSCs are particularly useful because they are highly proliferative and thus, can more quickly give rise to differentiated progeny.

As used herein, the term "hematopoietic stem cell functional potential" refers to the functional properties of hematopoietic stem cells which include 1) multi-potency (which refers to the ability to differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal (which refers to the ability of hematopoietic stem cells to give rise to daughter cells that have equivalent potential as the mother cell, and further that this ability can repeatedly occur throughout the lifetime of an individual without exhaustion), and 3) the ability of hematopoietic stem cells or progeny thereof to be reintroduced into a transplant recipient whereupon they home to the hematopoietic stem cell niche and re-establish productive and sustained hematopoiesis.

As used herein, the term "human antibody" refers to an antibody in which substantially every part of the protein (for example, all CDRs, framework regions, $C_L$, $C_H$ domains (e.g., $C_H1$, $C_H2$, $C_H3$), hinge, and $V_L$ and $V_H$ domains) is substantially non-immunogenic in humans, with only minor sequence changes or variations. A human antibody can be produced in a human cell (for example, by recombinant expression) or by a non-human animal or a prokaryotic or eukaryotic cell that is capable of expressing functionally rearranged human immunoglobulin (such as heavy chain and/or light chain) genes. When a human antibody is a single chain antibody, it can include a linker peptide that is not found in native human antibodies. For example, an Fv can contain a linker peptide, such as two to about eight glycine or other amino acid residues, which connects the variable region of the heavy chain and the variable region of the light chain. Such linker peptides are considered to be of human origin. Human antibodies can be made by a variety of methods known in the art including phage display methods using antibody libraries derived from human immunoglobulin sequences. Human antibodies can also be produced using transgenic mice that are incapable of expressing functional endogenous immunoglobulins, but which can express human immunoglobulin genes (see, for example, PCT Publication Nos. WO 1998/24893; WO 1992/01047; WO 1996/34096; WO 1996/33735; U.S. Pat. Nos. 5,413,923; 5,625, 126; 5,633,425; 5,569,825; 5,661,016; 5,545,806; 5,814, 318; 5,885,793; 5,916,771; and 5,939,598).

As used herein, the term "humanized" antibody refers to a non-human antibody that contains minimal sequences derived from non-human immunoglobulin. In general, a humanized antibody contains substantially all of at least one, and typically two, variable domains, in which all or substantially all of the CDR regions correspond to those of a non-human immunoglobulin. All or substantially all of the FW regions may also be those of a human immunoglobulin sequence. The humanized antibody can also contain at least a portion of an immunoglobulin constant region (Fc), typically that of a human immunoglobulin consensus sequence. Methods of antibody humanization are known in the art and have been described, for example, in Riechmann et al., Nature 332:323-7, 1988; U.S. Pat. Nos. 5,530,101; 5,585, 089; 5,693,761; 5,693,762; and 6,180,370.

As used herein, patients that are "in need of" a hematopoietic stem cell transplant include patients that exhibit a defect or deficiency in one or more blood cell types, as well as patients having a stem cell disorder, autoimmune disease, cancer, or other pathology described herein. Hematopoietic stem cells generally exhibit 1) multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells), 2) self-renewal, and can thus give rise to daughter cells that have equivalent potential as the mother cell, and 3) the ability to be reintroduced into a transplant recipient whereupon they home to the hematopoietic stem cell niche and re-establish productive and sustained hematopoiesis. Hematopoietic stem cells can thus be administered to a patient defective or deficient in one or more cell types of the hematopoietic lineage in order to re-constitute the defective or deficient population of cells in vivo. For example, the patient may be suffering from cancer, and the deficiency may be caused by administration of a chemotherapeutic agent or other medicament that depletes, either selectively or non-specifically, the cancerous cell population. Additionally or alternatively, the patient may be suffering from a hemoglobinopathy (e.g., a non-malignant hemoglobinopathy), such as sickle cell anemia, thalassemia, Fanconi anemia, aplastic anemia, and Wiskott-Aldrich syndrome. The subject may be one that is suffering from adenosine deaminase severe combined immunodeficiency (ADA SCID), HIV/AIDS, metachromatic leukodystrophy, Diamond-Blackfan anemia, and Schwachman-Diamond syndrome. The subject may have or be affected by an inherited blood disorder (e.g., sickle cell anemia) or an autoimmune disorder. Additionally or alternatively, the subject may have or be affected by a malignancy, such as neuroblastoma or a hematologic cancer. For instance, the subject may have a leukemia, lymphoma, or myeloma. In some embodiments, the subject has acute myeloid leukemia, acute lymphoid leukemia, chronic myeloid leukemia, chronic lymphoid leukemia, multiple myeloma, diffuse large B-cell lymphoma, or non-Hodgkin's lymphoma. In some embodiments, the subject has myelodysplastic syndrome. In some embodiments, the subject has an autoimmune disease, such as scleroderma, multiple sclerosis, ulcerative colitis, Crohn's disease, Type 1 diabetes, or another autoimmune pathology described herein. In some embodiments, the subject is in need of chimeric antigen receptor T-cell (CART) therapy. In some embodiments, the subject has or is otherwise affected by a metabolic storage disorder. The subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy. Additionally or alternatively, a patient "in need of" a hematopoietic stem cell transplant may one that is or is not suffering from one of the foregoing pathologies, but nonetheless exhibits a reduced level (e.g., as compared to that of an otherwise healthy subject) of one or more endogenous cell types within the hematopoietic lineage, such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes. One of skill in the art can readily determine whether one's level of one or more of the foregoing cell types, or other blood cell type, is reduced with respect to an otherwise healthy subject, for instance, by way of flow cytometry and fluorescence activated cell sorting (FACS) methods, among other procedures, known in the art.

As used herein, the term "monoclonal antibody" refers to an antibody that is derived from a single clone, including any eukaryotic, prokaryotic, or phage clone, and not the method by which it is produced.

As used herein, the term "recipient" refers to a patient that receives a transplant, such as a transplant containing a population of hematopoietic stem cells. The transplanted cells administered to a recipient may be, e.g., autologous, syngeneic, or allogeneic cells.

As used herein, the term "sample" refers to a specimen (e.g., blood, blood component (e.g., serum or plasma), urine, saliva, amniotic fluid, cerebrospinal fluid, tissue (e.g., placental or dermal), pancreatic fluid, chorionic villus sample, and cells) taken from a subject.

As used herein, the term "scFv" refers to a single chain Fv antibody in which the variable domains of the heavy chain and the light chain from an antibody have been joined to form one chain. scFv fragments contain a single polypeptide chain that includes the variable region of an antibody light chain ($V_L$) (e.g., CDR-L1, CDR-L2, and/or CDR-L3) and the variable region of an antibody heavy chain ($V_H$) (e.g., CDR-H1, CDR-H2, and/or CDR-H3) separated by a linker. The linker that joins the $V_L$ and $V_H$ regions of a scFv fragment can be a peptide linker composed of proteinogenic amino acids. Alternative linkers can be used to so as to increase the resistance of the scFv fragment to proteolytic degradation (for example, linkers containing D-amino acids), in order to enhance the solubility of the scFv fragment (for example, hydrophilic linkers such as polyethylene glycol-containing linkers or polypeptides containing repeating glycine and serine residues), to improve the biophysical stability of the molecule (for example, a linker containing cysteine residues that form intramolecular or intermolecular disulfide bonds), or to attenuate the immunogenicity of the scFv fragment (for example, linkers containing glycosylation sites). It will also be understood by one of ordinary skill in the art that the variable regions of the scFv molecules described herein can be modified such that they vary in amino acid sequence from the antibody molecule from which they were derived. For example, nucleotide or amino acid substitutions leading to conservative substitutions or changes at amino acid residues can be made (e.g., in CDR and/or framework residues) so as to preserve or enhance the ability of the scFv to bind to the antigen recognized by the corresponding antibody.

As used herein, the terms "subject" and "patient" refer to an organism, such as a human, that receives treatment for a particular disease or condition as described herein. For instance, a patient, such as a human patient, may receive treatment prior to hematopoietic stem cell transplant therapy in order to promote the engraftment of exogenous hematopoietic stem cells.

As used herein, the phrase "substantially cleared from the blood" refers to a point in time following administration of a therapeutic agent (such as an anti-CD117 antibody, antigen-binding fragment thereof, or ligand) to a patient when the concentration of the therapeutic agent in a blood sample isolated from the patient is such that the therapeutic agent is not detectable by conventional means (for instance, such that the therapeutic agent is not detectable above the noise threshold of the device or assay used to detect the therapeutic agent). A variety of techniques known in the art can be used to detect antibodies, antibody fragments, and protein ligands, such as ELISA-based detection assays known in the art or described herein. Additional assays that can be used to detect antibodies, antibody fragments, and protein ligands include immunoprecipitation techniques and immunoblot assays, among others known in the art.

As used herein, the phrase "stem cell disorder" broadly refers to any disease, disorder, or condition that may be treated or cured by conditioning a subject's target tissues, and/or by ablating an endogenous stem cell population in a target tissue (e.g., ablating an endogenous hematopoietic stem or progenitor cell population from a subject's bone marrow tissue) and/or by engrafting or transplanting stem cells in a subject's target tissues. For example, Type I diabetes has been shown to be cured by hematopoietic stem cell transplant and may benefit from conditioning in accordance with the compositions and methods described herein. Additional disorders that can be treated using the compositions and methods described herein include, without limitation, sickle cell anemia, thalassemias, Fanconi anemia, aplastic anemia, Wiskott-Aldrich syndrome, ADA SCID, HIV/AIDS, metachromatic leukodystrophy, Diamond-Blackfan anemia, and Schwachman-Diamond syndrome.

Additional diseases that may be treated using the patient conditioning and/or hematopoietic stem cell transplant methods described herein include inherited blood disorders (e.g., sickle cell anemia) and autoimmune disorders, such as scleroderma, multiple sclerosis, ulcerative colitis, and Crohn's disease. Additional diseases that may be treated using the conditioning and/or transplantation methods described herein include a malignancy, such as a neuroblastoma or a hematologic cancers, such as leukemia, lymphoma, and myeloma. For instance, the cancer may be acute myeloid leukemia, acute lymphoid leukemia, chronic myeloid leukemia, chronic lymphoid leukemia, multiple myeloma, diffuse large B-cell lymphoma, or non-Hodgkin's lymphoma. Additional diseases treatable using the conditioning and/or transplantation methods described herein include myelodysplastic syndrome. In some embodiments, the subject has or is otherwise affected by a metabolic storage disorder. For example, the subject may suffer or otherwise be affected by a metabolic disorder selected from the group consisting of glycogen storage diseases, mucopolysaccharidoses, Gaucher's Disease, Hurlers Disease, sphingolipidoses, metachromatic leukodystrophy, or any other diseases or disorders which may benefit from the treatments and therapies disclosed herein and including, without limitation, severe combined immunodeficiency, Wiscott-Aldrich syndrome, hyper immunoglobulin M (IgM) syndrome, Chediak-Higashi disease, hereditary lymphohistiocytosis, osteopetrosis, osteogenesis imperfecta, storage diseases, thalassemia major, sickle cell disease, systemic sclerosis, systemic lupus erythematosus, multiple sclerosis, juvenile rheumatoid arthritis and those diseases, or disorders described in "Bone Marrow Transplantation for Non-Malignant Disease," ASH Education Book, 1:319-338 (2000), the disclosure of which is incorporated herein by reference in its entirety as it pertains to pathologies that may be treated by administration of hematopoietic stem cell transplant therapy.

As used herein, the term "transfection" refers to any of a wide variety of techniques commonly used for the introduction of exogenous DNA into a prokaryotic or eukaryotic host cell, such as electroporation, lipofection, calcium-phosphate precipitation, DEAE-dextran transfection and the like.

As used herein, the terms "treat" or "treatment" refer to therapeutic treatment, in which the object is to prevent or slow down (lessen) an undesired physiological change or disorder or to promote a beneficial phenotype in the patient being treated. Beneficial or desired clinical results include, but are not limited to, promoting the engraftment of exogenous hematopoietic cells in a patient following antibody conditioning therapy as described herein and subsequent hematopoietic stem cell transplant therapy. Additional beneficial results include an increase in the cell count or relative concentration of hematopoietic stem cells in a patient in need of a hematopoietic stem cell transplant following conditioning therapy and subsequent administration of an exogenous hematopoietic stem cell graft to the patient. Beneficial results of therapy described herein may also include an increase in the cell count or relative concentration of one or more cells of hematopoietic lineage, such as a megakaryocyte, thrombocyte, platelet, erythrocyte, mast cell, myeoblast, basophil, neutrophil, eosinophil, microglial cell, granulocyte, monocyte, osteoclast, antigen-presenting cell, macrophage, dendritic cell, natural killer cell, T-lymphocyte, or B-lymphocyte, following conditioning therapy and subsequent hematopoietic stem cell transplant therapy. Additional beneficial results may include the reduction in quantity of a disease-causing cell population, such as a population of cancer cells (e.g., CD117+ leukemic cells) or autoimmune cells (e.g., CD117+ autoimmune lymphocytes, such as a CD117+ T-cell that expresses a T-cell receptor that cross-reacts with a self antigen).

As used herein, the terms "variant" and "derivative" are used interchangeably and refer to naturally-occurring, synthetic, and semi-synthetic analogues of a compound, peptide, protein, or other substance described herein. A variant or derivative of a compound, peptide, protein, or other substance described herein may retain or improve upon the biological activity of the original material.

As used herein, the term "vector" includes a nucleic acid vector, such as a plasmid, a DNA vector, a plasmid, a RNA vector, virus, or other suitable replicon. Expression vectors described herein may contain a polynucleotide sequence as well as, for example, additional sequence elements used for the expression of proteins and/or the integration of these polynucleotide sequences into the genome of a mammalian cell. Certain vectors that can be used for the expression of antibodies and antibody fragments of the invention include plasmids that contain regulatory sequences, such as promoter and enhancer regions, which direct gene transcription. Other useful vectors for expression of antibodies and antibody fragments contain polynucleotide sequences that enhance the rate of translation of these genes or improve the stability or nuclear export of the mRNA that results from gene transcription. These sequence elements may include, for example, 5' and 3' untranslated regions and a polyadenylation signal site in order to direct efficient transcription of the gene carried on the expression vector. The expression vectors described herein may also contain a polynucleotide encoding a marker for selection of cells that contain such a vector. Examples of a suitable marker include genes that encode resistance to antibiotics, such as ampicillin, chloramphenicol, kanamycin, and nourseothricin.

As used herein, the term "alkyl" refers to a straight- or branched-chain alkyl group having, for example, from 1 to 20 carbon atoms in the chain. Examples of alkyl groups include methyl, ethyl, n-propyl, isopropyl, butyl, isobutyl, sec-butyl, tert-butyl, pentyl, isopentyl, tert-pentyl, hexyl, isohexyl, and the like.

As used herein, the term "alkylene" refers to a straight- or branched-chain divalent alkyl group. The divalent positions may be on the same or different atoms within the alkyl chain. Examples of alkylene include methylene, ethylene, propylene, isopropylene, and the like.

As used herein, the term "heteroalkyl" refers to a straight or branched-chain alkyl group having, for example, from 1 to 20 carbon atoms in the chain, and further containing one or more heteroatoms (e.g., oxygen, nitrogen, or sulfur, among others) in the chain.

As used herein, the term "heteroalkylene" refers to a straight- or branched-chain divalent heteroalkyl group. The divalent positions may be on the same or different atoms within the heteroalkyl chain. The divalent positions may be one or more heteroatoms.

As used herein, the term "alkenyl" refers to a straight- or branched-chain alkenyl group having, for example, from 2 to 20 carbon atoms in the chain. Examples of alkenyl groups include vinyl, propenyl, isopropenyl, butenyl, tert-butylenyl, hexenyl, and the like.

As used herein, the term "alkenylene" refers to a straight- or branched-chain divalent alkenyl group. The divalent positions may be on the same or different atoms within the alkenyl chain. Examples of alkenylene include ethenylene, propenylene, isopropenylene, butenylene, and the like.

As used herein, the term "heteroalkenyl" refers to a straight- or branched-chain alkenyl group having, for example, from 2 to 20 carbon atoms in the chain, and further containing one or more heteroatoms (e.g., oxygen, nitrogen, or sulfur, among others) in the chain.

As used herein, the term "heteroalkenylene" refers to a straight- or branched-chain divalent heteroalkenyl group. The divalent positions may be on the same or different atoms within the heteroalkenyl chain. The divalent positions may be one or more heteroatoms.

As used herein, the term "alkynyl" refers to a straight- or branched-chain alkynyl group having, for example, from 2 to 20 carbon atoms in the chain. Examples of alkynyl groups include propargyl, butynyl, pentynyl, hexynyl, and the like.

As used herein, the term "alkynylene" refers to a straight- or branched-chain divalent alkynyl group. The divalent positions may be on the same or different atoms within the alkynyl chain.

As used herein, the term "heteroalkynyl" refers to a straight- or branched-chain alkynyl group having, for example, from 2 to 20 carbon atoms in the chain, and further containing one or more heteroatoms (e.g., oxygen, nitrogen, or sulfur, among others) in the chain.

As used herein, the term "heteroalkynylene" refers to a straight- or branched-chain divalent heteroalkynyl group. The divalent positions may be on the same or different atoms within the heteroalkynyl chain. The divalent positions may be one or more heteroatoms.

As used herein, the term "cycloalkyl" refers to a monocyclic, or fused, bridged, or spiro polycyclic ring structure that is saturated and has, for example, from 3 to 12 carbon ring atoms. Examples of cycloalkyl groups include cyclopropyl, cyclobutyl, cyclopentyl, cyclohexyl, cycloheptyl, cyclooctyl, bicyclo[3.1.0]hexane, and the like.

As used herein, the term "cycloalkylene" refers to a divalent cycloalkyl group. The divalent positions may be on the same or different atoms within the ring structure. Examples of cycloalkylene include cyclopropylene, cyclobutylene, cyclopentylene, cyclohexylene, and the like.

As used herein, the term "heterocyloalkyl" refers to a monocyclic, or fused, bridged, or spiro polycyclic ring structure that is saturated and has, for example, from 3 to 12 ring atoms per ring structure selected from carbon atoms and heteroatoms selected from, e.g., nitrogen, oxygen, and sulfur, among others. The ring structure may contain, for example, one or more oxo groups on carbon, nitrogen, or sulfur ring members.

As used herein, the term "heterocycloalkylene" refers to a divalent heterocyclolalkyl group. The divalent positions may be on the same or different atoms within the ring structure.

As used herein, the term "aryl" refers to a monocyclic or multicyclic aromatic ring system containing, for example, from 6 to 19 carbon atoms. Aryl groups include, but are not limited to, phenyl, fluorenyl, naphthyl, and the like. The divalent positions may be one or more heteroatoms.

As used herein, the term "arylene" refers to a divalent aryl group. The divalent positions may be on the same or different atoms.

As used herein, the term "heteroaryl" refers to a monocyclic heteroaromatic, or a bicyclic or a tricyclic fused-ring heteroaromatic group. Heteroaryl groups include pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a] pyridyl, benzothiazolyl, benzoxazolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl, benzoquinolyl, and the like.

As used herein, the term "heteroarylene" refers to a divalent heteroaryl group. The divalent positions may be on the same or different atoms. The divalent positions may be one or more heteroatoms.

Unless otherwise constrained by the definition of the individual substituent, the foregoing chemical moieties, such as "alkyl", "alkylene", "heteroalkyl", "heteroalkylene", "alkenyl", "alkenylene", "heteroalkenyl", "heteroalkenylene", "alkynyl", "alkynylene", "heteroalkynyl", "heteroalkynylene", "cycloalkyl", "cycloalkylene", "heterocyclolalkyl", heterocycloalkylene", "aryl," "arylene", "heteroaryl", and "heteroarylene" groups can optionally be substituted with, for example, from 1 to 5 substituents selected from the group consisting of alkyl, alkenyl, alkynyl, cycloalkyl, heterocycloalkyl, alkyl aryl, alkyl heteroaryl, alkyl cycloalkyl, alkyl heterocycloalkyl, amino, ammonium, acyl, acyloxy, acylamino, aminocarbonyl, alkoxycarbonyl, ureido, carbamate, aryl, heteroaryl, sulfinyl, sulfonyl, alkoxy, sulfanyl, halogen, carboxy, trihalomethyl, cyano, hydroxy, mercapto, nitro, and the like. The substitution may include situations in which neighboring substituents have undergone ring closure, such as ring closure of vicinal functional substituents, to form, for instance, lactams, lactones, cyclic anhydrides, acetals, hemiacetals, thioacetals, aminals, and hemiaminals, formed by ring closure, for example, to furnish a protecting group.

Anti-CD117 Antibodies and Ligands

The present invention is based in part on the discovery that antibodies, antigen-binding fragments thereof, and ligands capable of binding CD117, such as GNNK+CD117, can be used as therapeutic agents to (i) directly treat cancers and autoimmune diseases characterized by CD117+ cells and (ii) promote the engraftment of transplanted hematopoietic stem cells in a patient in need of transplant therapy. These therapeutic activities can be caused, for instance, by the binding of anti-CD117 antibodies, antigen-binding fragments thereof, and/or ligands to CD117 (e.g., GNNK+ CD117) expressed on the surface of a cell, such as a cancer cell, autoimmune cell, or hematopoietic stem cell and subsequently inducing cell death. The depletion of endogenous hematopoietic stem cells can provide a niche toward which transplanted hematopoietic stem cells can home, and subsequently establish productive hematopoiesis. In this way, transplanted hematopoietic stem cells may successfully engraft in a patient, such as human patient suffering from a stem cell disorder described herein.

Antibodies and antigen-binding fragments capable of binding human CD117 (also referred to as c-Kit, mRNA NCBI Reference Sequence: NM_000222.2, Protein NCBI Reference Sequence: NP_000213.1), including those capable of binding GNNK+CD117, can be used in conjunction with the compositions and methods described herein in order to condition a patient for hematopoietic stem cell transplant therapy. Polymorphisms affecting the coding region or extracellular domain of CD117 in a significant percentage of the population are not currently well-known in non-oncology indications. There are at least four isoforms of CD117 that have been identified, with the potential of additional isoforms expressed in tumor cells. Two of the CD117 isoforms are located on the intracellular domain of the protein, and two are present in the external juxtamembrane region. The two extracellular isoforms, GNNK+ and GNNK−, differ in the presence (GNNK+) or absence (GNNK−) of a 4 amino acid sequence. These isoforms are reported to have the same affinity for the ligand (SCF), but ligand binding to the GNNK− isoform was reported to increase internalization and degradation. The GNNK+ isoform can be used as an immunogen in order to generate antibodies capable of binding CD117, as antibodies generated against this isoform will be inclusive of the GNNK+ and GNNK− proteins.

Anti-CD117 antibodies that can be used in conjunction with the patient conditioning methods described herein include, for instance, antibodies produced and released from ATCC Accession No. 10716 (deposited as BA7.3C.9), such as the SR-1 antibody, which is described, for example, in U.S. Pat. No. 5,489,516, the disclosure of which is incorporated herein by reference as it pertains to anti-CD117 antibodies.

Additional anti-CD117 antibodies that can be used in conjunction with the patient conditioning methods described herein include those described in U.S. Pat. No. 7,915,391, which describes, e.g., humanized SR-1 antibodies; U.S. Pat. No. 5,808,002, which describes, e.g., the anti-CD117 A3C6E2 antibody, as well as those described in, for example, WO 2015/050959, which describes anti-CD117 antibodies that bind epitopes containing Pro317, Asn320, Glu329, Val331, Asp332, Lus358, Glue360, Glue376, His378, and/or Thr380 of human CD117; and US 2012/0288506 (also published as U.S. Pat. No. 8,552,157), which describes, e.g., the anti-CD117 antibody CK6, having the CDR sequences of:
  a. a CDR-H1 having the amino acid sequence SYWIG (SEQ ID NO: 1);
  b. a CDR-H2 having the amino acid sequence IIYPGDSDTRYSPSFQG (SEQ ID NO: 2);
  c. a CDR-H3 having the amino acid sequence HGRGYNGYEGAFDI (SEQ ID NO: 3);
  d. a CDR-L1 having the amino acid sequence RASQGISSALA (SEQ ID NO: 4);
  e. a CDR-L2 having the amino acid sequence DASSLES (SEQ ID NO: 5); and
  f. a CDR-L3 having the amino acid sequence CQQFNSYPLT (SEQ ID NO: 6).

Additional anti-CD117 antibodies and antigen-binding fragments thereof that may be used in conjunction with the compositions and methods described herein include those described in US 2015/0320880, such as the clones 9P3, NEG024, NEG027, NEG085, NEG086, and 20376.

The disclosures of each of the foregoing publications are incorporated herein by reference as they pertain to anti-CD117 antibodies. Antibodies and antigen-binding fragments that may be used in conjunction with the compositions and methods described herein include the above-described antibodies and antigen-binding fragments thereof, as well as humanized variants of those non-human antibodies and antigen-binding fragments described above and antibodies or antigen-binding fragments that bind the same epitope as those described above, as assessed, for instance, by way of a competitive CD117 binding assay.

Additional Antibodies and Antigen-Binding Fragments Thereof

Antibodies and ligands for use in conjunction with the methods described herein include variants of those antibodies described above, such as antibody fragments that contain or lack an Fc domain, as well as humanized variants of non-human antibodies described herein and antibody-like protein scaffolds (e.g., $^{10}$Fn3 domains) containing one or more, or all, of the CDRs or equivalent regions thereof of an antibody, antibody fragment, or ligand described herein. Exemplary antigen-binding fragments of the foregoing antibodies include a dual-variable immunoglobulin domain, a single-chain Fv molecule (scFv), a diabody, a triabody, a nanobody, an antibody-like protein scaffold, a Fv fragment, a Fab fragment, a F(ab')$_2$ molecule, and a tandem di-scFv, among others.

Methods of Identifying Antibodies and Ligands

Methods for high throughput screening of antibody, antibody fragment, and ligand libraries for molecules capable of binding CD117 (e.g., GNNK+CD117) can be used to identify and affinity mature antibodies useful for treating cancers, autoimmune diseases, and conditioning a patient (e.g., a human patient) in need of hematopoietic stem cell therapy as described herein. Such methods include in vitro display techniques known in the art, such as phage display, bacterial display, yeast display, mammalian cell display, ribosome display, mRNA display, and cDNA display, among others. The use of phage display to isolate ligands that bind biologically relevant molecules has been reviewed, for example, in Felici et al., Biotechnol. Annual Rev. 1:149-183, 1995; Katz, Annual Rev. Biophys. Biomol. Struct. 26:27-45, 1997; and Hoogenboom et al., Immunotechnology 4:1-20, 1998, the disclosures of each of which are incorporated herein by reference as they pertain to in vitro display techniques. Randomized combinatorial peptide libraries have been constructed to select for polypeptides that bind cell surface antigens as described in Kay, Perspect. Drug Discovery Des. 2:251-268, 1995 and Kay et al., Mol. Divers. 1:139-140, 1996, the disclosures of each of which are incorporated herein by reference as they pertain to the discovery of antigen-binding molecules. Proteins, such as multimeric proteins, have been successfully phage-displayed as functional molecules (see, for example, EP 0349578; EP 4527839; and EP 0589877, as well as Chiswell and McCafferty, Trends Biotechnol. 10:80-84 1992, the disclosures of each of which are incorporated herein by reference as they pertain to the use of in vitro display techniques for the discovery of antigen-binding molecules). In addition, functional antibody fragments, such as Fab and scFv fragments, have been expressed in in vitro display formats (see, for example, McCafferty et al., Nature 348: 552-554, 1990; Barbas et al., Proc. Natl. Acad. Sci. USA 88:7978-7982, 1991; and Clackson et al., Nature 352:624-628, 1991, the disclosures of each of which are incorporated herein by reference as they pertain to in vitro display platforms for the discovery of antigen-binding molecules). These techniques, among others, can be used to identify and improve the affinity of antibodies that bind CD117 (e.g., GNNK+CD117) that can in turn be used to deplete endogenous hematopoietic stem cells in a patient (e.g., a human patient) in need of hematopoietic stem cell transplant therapy.

In addition to in vitro display techniques, computational modeling techniques can be used to design and identify antibodies, antibody fragments, and ligands in silico that bind CD117 (e.g., GNNK+CD117). For example, using computational modeling techniques, one of skill in the art can screen libraries of antibodies, antibody fragments, and ligands in silico for molecules capable of binding specific epitopes, such as extracellular epitopes of this antigen. The antibodies, antigen-binding fragments thereof, and ligands identified by these computational techniques can be used in conjunction with the therapeutic methods described herein, such as the cancer and autoimmune disease treatment methods described herein and the patient conditioning procedures described herein.

Additional techniques can be used to identify antibodies, antigen-binding fragments thereof, and ligands that bind CD117 (e.g., GNNK+CD117) on the surface of a cell (e.g., a cancer cell, autoimmune cell, or hematopoietic stem cell) and that are internalized by the cell, for instance, by receptor-mediated endocytosis. For example, the in vitro display techniques described above can be adapted to screen for antibodies, antigen-binding fragments thereof, and ligands that bind CD117 (e.g., GNNK+CD117) on the surface of a cancer cell, autoimmune cell, or hematopoietic stem cell and that are subsequently internalized. Phage display represents one such technique that can be used in conjunction with this screening paradigm. To identify antibodies, fragments thereof, and ligands that bind CD117 (e.g., GNNK+CD117) and are subsequently internalized by cancer cells, autoimmune cells, or hematopoietic stem cells, one of skill in the art can adapt the phage display techniques described, for example, in Williams et al., Leukemia 19:1432-1438, 2005, the disclosure of which is incorporated herein by reference in its entirety. For example, using mutagenesis methods known in the art, recombinant phage libraries can be produced that encode antibodies, antibody fragments, such as scFv fragments, Fab fragments, diabodies, triabodies, and $^{10}$Fn3 domains, among others, or ligands that contain randomized amino acid cassettes (e.g., in one or more, or all, of the CDRs or equivalent regions thereof or an antibody or antibody fragment). The framework regions, hinge, Fc domain, and other regions of the antibodies or antibody fragments may be designed such that they are non-immunogenic in humans, for instance, by virtue of having human germline antibody sequences or sequences that exhibit only minor variations relative to human germline antibodies.

Using phage display techniques described herein or known in the art, phage libraries containing randomized antibodies, antibody fragments, or ligands covalently bound to the phage particles can be incubated with CD117 (e.g., GNNK+CD117) antigen, for instance, by first incubating the phage library with blocking agents (such as, for instance, milk protein, bovine serum albumin, and/or IgG so as to remove phage encoding antibodies, fragments thereof, or ligands that exhibit non-specific protein binding and phage that encode antibodies or fragments thereof that bind Fc domains, and then incubating the phage library with a population of hematopoietic stem cells. The phage library can be incubated with the target cells, such as cancer cells, autoimmune cells, or hematopoietic stem cells for a time sufficient to allow CD117-specific antibodies, antigen-binding fragments thereof, or ligands (e.g., GNNK+CD117-specific antibodies, antigen-binding fragments thereof, or ligands) to bind cell-surface CD117 (e.g., sell-surface GNNK+CD117) antigen and to subsequently be internalized by the cancer cells, autoimmune cells, or hematopoietic stem cells (e.g., from 30 minutes to 6 hours at 4° C., such as 1 hour at 4° C.). Phage containing antibodies, fragments thereof, or ligands that do not exhibit sufficient affinity for one or more of these antigens so as to permit binding to, and internalization by, cancer cells, autoimmune cells, or hematopoietic stem cells can subsequently be removed by washing the cells, for instance, with cold (4° C.) 0.1 M glycine buffer at pH 2.8. Phage bound to antibodies, fragments thereof, or ligands that have been internalized by the cancer cells, autoimmune cells, or hematopoietic stem cells can be identified, for instance, by lysing the cells and recovering internalized phage from the cell culture medium.

The phage can then be amplified in bacterial cells, for example, by incubating bacterial cells with recovered phage in 2×YT medium using methods known in the art. Phage recovered from this medium can then be characterized, for instance, by determining the nucleic acid sequence of the gene(s) encoding the antibodies, fragments thereof, or ligands inserted within the phage genome. The encoded antibodies, fragments thereof, or ligands can subsequently be prepared de novo by chemical synthesis (for instance, of antibody fragments, such as scFv fragments, or ligands) or by recombinant expression (for instance, of full-length antibodies).

The internalizing capacity of the prepared antibodies, fragments thereof, or ligands can be assessed, for instance, using radionuclide internalization assays known in the art. For example, antibodies, fragments thereof, or ligands identified using in vitro display techniques described herein or known in the art can be functionalized by incorporation of a radioactive isotope, such as $^{18}$F, $^{75}$Br, $^{77}$Br, $^{122}$I, $^{123}$I, $^{124}$I, $^{125}$I, $^{129}$I, $^{131}$I, $^{211}$At, $^{67}$Ga, $^{111}$In, $^{99}$Tc, $^{169}$Yb, $^{186}$Re, $^{64}$Cu, $^{67}$Cu, $^{177}$Lu, $^{77}$As, $^{72}$As, $^{86}$Y, $^{90}$Y, $^{89}$Zr, $^{212}$Bi, $^{213}$Bi, or $^{225}$Ac. For instance, radioactive halogens, such as $^{18}$F, $^{75}$Br, $^{77}$Br, $^{122}$I, $^{123}$I, $^{124}$I, $^{125}$I, $^{129}$I, $^{131}$I, $^{211}$At, can be incorporated into antibodies, fragments thereof, or ligands using beads, such as polystyrene beads, containing electrophilic halogen reagents (e.g., Iodination Beads, Thermo Fisher Scientific, Inc., Cambridge, Mass.). Radiolabeled antibodies, fragments thereof, or ligands can be incubated with cancer cells, autoimmune cells, or hematopoietic stem cells for a time sufficient to permit internalization (e.g., from 30 minutes to 6 hours at 4° C., such as 1 hour at 4° C.). The cells can then be washed to remove non-internalized antibodies, fragments thereof, or ligands (e.g., using cold (4° C.) 0.1 M glycine buffer at pH 2.8). Internalized antibodies, fragments thereof, or ligands can be identified by detecting the emitted radiation (e.g., γ-radiation) of the resulting cancer cells, autoimmune cells, or hematopoietic stem cells in comparison with the emitted radiation (e.g., γ-radiation) of the recovered wash buffer.

Drug-Antibody Conjugates and Drug-Ligand Conjugates

Cytotoxins

Antibodies, antigen-binding fragments thereof, and ligands described herein (e.g., antibodies, antigen-binding fragments, and ligands that recognize and bind CD117 (such as GNNK+CD117) can be conjugated to a cytotoxin, such as pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, and an indolinobenzodiazepine dimer, or a variant thereof, or another cytotoxic compound described herein or known in the art, for example, in order to treat a cancer or autoimmune disease described herein or to promote the depletion of endogenous hematopoietic stem cells upon administration to a patient (e.g., a human patient) in need of hematopoietic stem cell transplant therapy. In some embodiments, the cytotoxic molecule is conjugated to an internalizing antibody, antigen-binding fragment thereof, or ligand, such that following the cellular uptake of the antibody, antigen-binding fragment, or ligand, the cytotoxin may access its intracellular target and mediate endogenous hematopoietic cell death. Cytotoxins suitable for use with the compositions and methods described herein include DNA-intercalating agents, (e.g., anthracyclines), agents capable of disrupting the mitotic spindle apparatus (e.g., vinca alkaloids, maytansine, maytansinoids, and derivatives thereof), RNA polymerase inhibitors (e.g., an amatoxin, such as α-amanitin and derivatives thereof), agents capable of disrupting protein biosynthesis (e.g., agents that exhibit rRNA N-glycosidase activity, such as saporin and ricin A-chain), among others known in the art.

In some embodiments, the cytotoxin is an amatoxin or derivative thereof, such as α-amanitin, β-amanitin, γ-amanitin, ε-amanitin, amanin, amaninamide, amanullin, amanullinic acid, and proamanullin. For instance, the antibodies, antigen-binding fragments, and ligands described herein may be bound to an amatoxin so as to form a conjugate represented by the formula Ab-Am, wherein Ab is the antibody, antigen-binding fragment thereof, or ligand, and Am is an amatoxin. In some embodiments, Am is represented by formula (I)

(e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene; and Z is a chemical moiety formed from a coupling reaction between a reactive substituent present on L and a reactive substituent present within an antibody, antigen-binding fragment thereof, or ligand that binds CD117 (such as GNNK+ CD117).

In some embodiments, Am contains exactly one $R_C$ substituent.

In some embodiments, Am is represented by formula (IA)

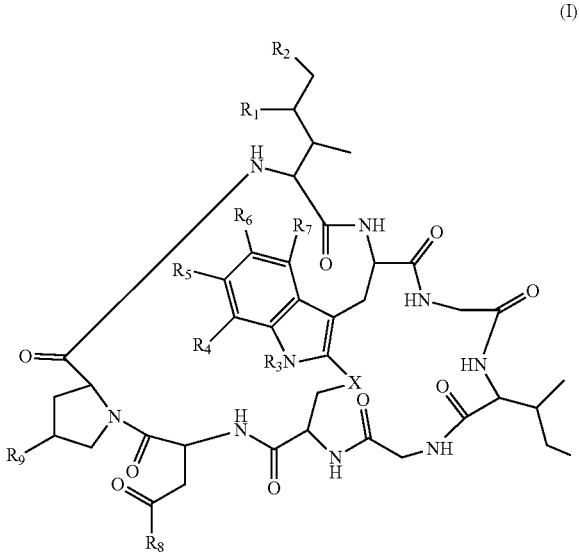

(I)

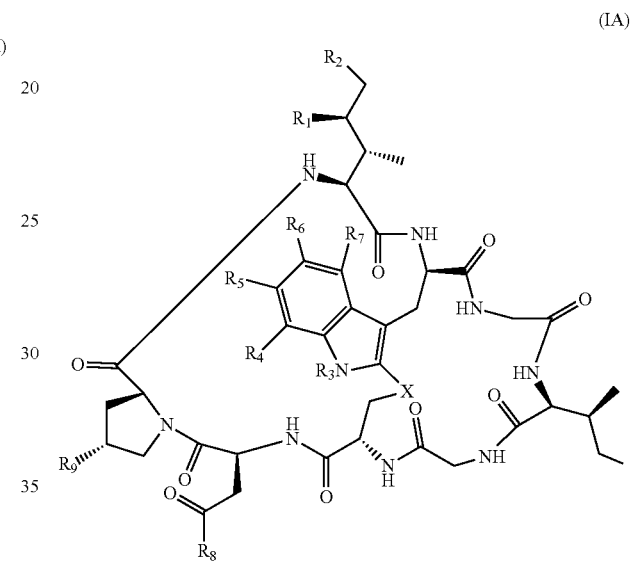

(IA)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;
L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene;

Z is a chemical moiety formed from a coupling reaction between a reactive substituent present on L and a reactive substituent present within an antibody, antigen-binding fragment thereof, or ligand that binds CD117 (such as GNNK+ CD117); and wherein Am contains exactly one $R_C$ substituent.

In some embodiments, Am is represented by formula (IB)

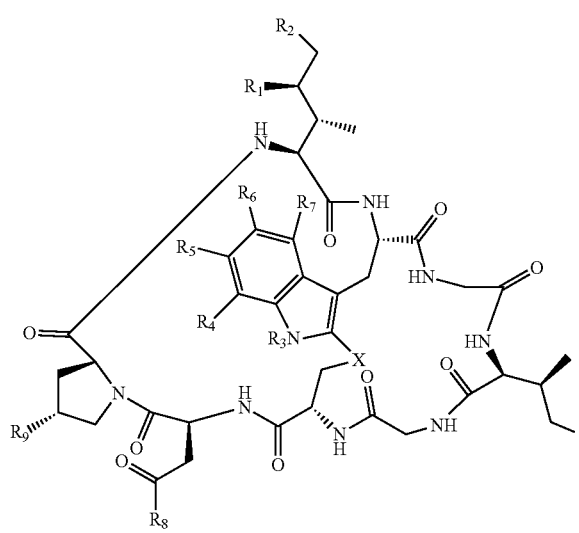

(IB)

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocyclolalkyl group;
$R_3$ is H, $R_C$, or $R_D$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —SO$_2$—;
$R_C$ is -L-Z;
$R_D$ is optionally substituted alkyl (e.g., $C_1$-$C_6$ alkyl), optionally substituted heteroalkyl (e.g., $C_1$-$C_6$ heteroalkyl), optionally substituted alkenyl (e.g., $C_2$-$C_6$ alkenyl), optionally substituted heteroalkenyl (e.g., $C_2$-$C_6$ heteroalkenyl), optionally substituted alkynyl (e.g., $C_2$-$C_6$ alkynyl), optionally substituted heteroalkynyl (e.g., $C_2$-$C_6$ heteroalkynyl), optionally substituted cycloalkyl, optionally substituted heterocycloalkyl, optionally substituted aryl, or optionally substituted heteroaryl;

L is a linker, such as optionally substituted alkylene (e.g., $C_1$-$C_6$ alkylene), optionally substituted heteroalkylene ($C_1$-$C_6$ heteroalkylene), optionally substituted alkenylene (e.g., $C_2$-$C_6$ alkenylene), optionally substituted heteroalkenylene (e.g., $C_2$-$C_6$ heteroalkenylene), optionally substituted alkynylene (e.g., $C_2$-$C_6$ alkynylene), optionally substituted heteroalkynylene (e.g., $C_2$-$C_6$ heteroalkynylene), optionally substituted cycloalkylene, optionally substituted heterocycloalkylene, optionally substituted arylene, or optionally substituted heteroarylene;

Z is a chemical moiety formed from a coupling reaction between a reactive substituent present on L and a reactive substituent present within an antibody, antigen-binding fragment thereof, or ligand that binds CD117 (such as GNNK+ CD117); and wherein Am contains exactly one $R_C$ substituent.

In some embodiments, $R_A$ and $R_B$, together with the oxygen atoms to which they are bound, combine to form:

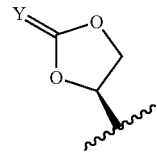

wherein Y is selected from O, S, $NR_E$, and $CR_ER_{E'}$, and $R_E$ and $R_{E'}$ are each independently optionally substituted $C_1$-$C_6$ alkylene-$R_C$, optionally substituted $C_1$-$C_6$ heteroalkylene-$R_C$, optionally substituted $C_2$-$C_6$ alkenylene-$R_C$, optionally substituted $C_2$-$C_6$ heteroalkenylene-$R_C$, optionally substituted $C_2$-$C_6$ alkynylene-$R_C$, optionally substituted $C_2$-$C_6$ heteroalkynylene-$R_C$, optionally substituted cycloalkylene-$R_C$, optionally substituted heterocycloalkylene-$R_C$, optionally substituted arylene-$R_C$, or optionally substituted heteroarylene-$R_C$.

In some embodiments, Am is represented by formula (IA) or formula (IB),
wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form:

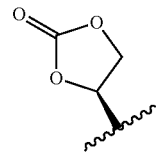 [SMILES: *[C@@H]1COC(=O)O1]

$R_3$ is H or $R_C$;
$R_4$ is H, OH, $OR_C$, $OR_D$, $R_C$, or $R_D$;
$R_5$ is H, OH, $OR_C$, $OR_D$, $R_C$, or $R_D$;
$R_6$ is H, OH, $OR_C$, $OR_D$, $R_C$, or $R_D$;
$R_7$ is H, OH, $OR_C$, $OR_D$, $R_C$, or $R_D$;
$R_8$ is OH, $NH_2$, $OR_C$, or $NHR_C$;
$R_9$ is H or OH; and
wherein $R_C$ and $R_D$ are each as defined above.

In some embodiments, Am is represented by formula (IA) or formula (IB),
wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form:

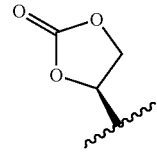 [SMILES: *[C@@H]1COC(=O)O1]

$R_3$ is H or $R_C$;
$R_4$ and $R_5$ are each independently H, OH, $OR_C$, $R_C$, or $OR_D$;
$R_6$ and $R_7$ are each H;
$R_8$ is OH, $NH_2$, $OR_C$, or $NHR_C$;
$R_9$ is H or OH; and
wherein $R_C$ is as defined above.

In some embodiments, Am is represented by formula (IA) or formula (IB),
wherein $R_1$ is H, OH, or $OR_A$;
$R_2$ is H, OH, or $OR_B$;
$R_A$ and $R_B$, together with the oxygen atoms to which they are bound, combine to form:

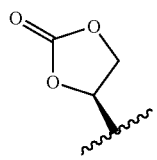 [SMILES: *[C@@H]1COC(=O)O1]

$R_3$, $R_4$, $R_6$, and $R_7$ are each H;
$R_5$ is $OR_C$;
$R_8$ is OH or $NH_2$;
$R_9$ is H or OH; and
wherein $R_C$ is as defined above. Such amatoxin conjugates are described, for example, in US Patent Application Publication No. 2016/0002298, the disclosure of which is incorporated herein by reference in its entirety.

In some embodiments, Am is represented by formula (IA) or formula (IB), wherein $R_1$ and $R_2$ are each independently H or OH;
$R_3$ is $R_C$;
$R_4$, $R_6$, and $R_7$ are each H;
$R_5$ is H, OH, or $OC_1$-$C_6$ alkyl;
$R_8$ is OH or $NH_2$;
$R_9$ is H or OH; and
wherein $R_C$ is as defined above. Such amatoxin conjugates are described, for example, in US Patent Application Publication No. 2014/0294865, the disclosure of which is incorporated herein by reference in its entirety.

In some embodiments, Am is represented by formula (IA) or formula (IB),
wherein $R_1$ and $R_2$ are each independently H or OH;
$R_3$, $R_6$, and $R_7$ are each H;
$R_4$ and $R_5$ are each independently H, OH, $OR_C$, or $R_C$;
$R_8$ is OH or $NH_2$;
$R_9$ is H or OH; and
wherein $R_C$ is as defined above. Such amatoxin conjugates are described, for example, in US Patent Application Publication No. 2015/0218220, the disclosure of which is incorporated herein by reference in its entirety.

In some embodiments, Am is represented by formula (IA) or formula (IB),
wherein $R_1$ and $R_2$ are each independently H or OH;
$R_3$, $R_6$, and $R_7$ are each H;
$R_4$ and $R_5$ are each independently H or OH;
$R_8$ is OH, $NH_2$, $OR_C$, or $NHR_C$;
$R_9$ is H or OH; and
wherein $R_C$ is as defined above. Such amatoxin conjugates are described, for example, in U.S. Pat. Nos. 9,233,173 and 9,399,681, as well as in US 2016/0089450, the disclosures of each of which are incorporated herein by reference in their entirety.

Additional amatoxins that may be used for conjugation to an antibody, antigen-binding fragment thereof, or ligand in accordance with the compositions and methods described herein are described, for example, in WO 2016/142049; WO 2016/071856; and WO 2017/046658, the disclosures of each of which are incorporated herein by reference in their entirety.

In some embodiments, Am is represented by formula (II),

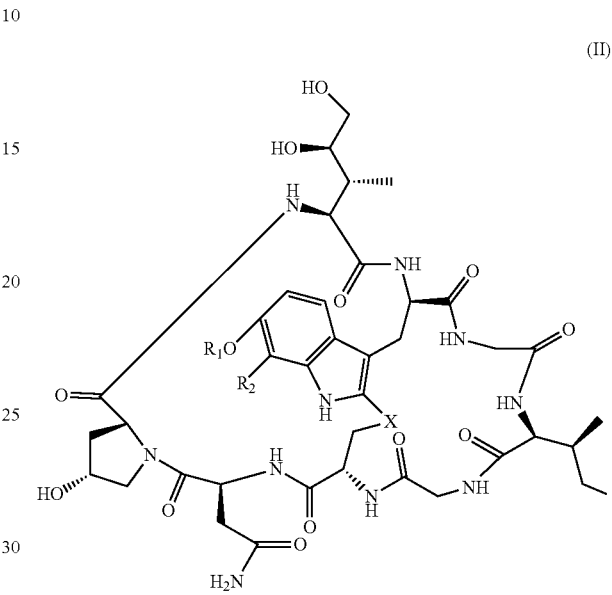

wherein X is S, SO, or $SO_2$;
$R_1$ is H or a linker covalently bound to the antibody or antigen-binding fragment thereof;
$R_2$ is H or a linker covalently bound to the antibody or antigen-binding fragment thereof; and
wherein when $R_1$ is H, $R_2$ is the linker, and when $R_2$ is H, $R_1$ is the linker.

Antibodies, antigen-binding fragments, and ligands for use with the compositions and methods described herein can be conjugated to an amatoxin, such as α-amanitin or a variant thereof, using conjugation techniques known in the art or described herein. For instance, antibodies, antigen-binding fragments thereof, and ligands that recognize and bind CD117 (such as GNNK+CD117) can be conjugated to an amatoxin, such as α-amanitin or a variant thereof, as described in US 2015/0218220, the disclosure of which is incorporated herein by reference as it pertains, for example, to amatoxins, such as α-amanitin and variants thereof, as well as covalent linkers that can be used for covalent conjugation.

Exemplary antibody-drug and ligand-drug conjugates useful in conjunction with the methods described herein may be formed by the reaction of an antibody, antigen-binding fragment thereof, or ligand with an amatoxin that is conjugated to a linker containing a substituent suitable for reaction with a reactive residue on the antibody, antigen-binding fragment thereof, or ligand. Amatoxins that are conjugated to a linker containing a substituent suitable for reaction with a reactive residue on the antibody, antigen-binding fragment thereof, or ligand described herein include, without limitation, 7'C-(4-(6-(maleimido)hexanoyl)piperazin-1-yl)-amatoxin; 7'C-(4-(6-(maleimido)hexanamido)piperidin-1-yl)-amatoxin; 7'C-(4-(6-(6-(maleimido)hexanamido)hexanoyl) piperazin-1-yl)-amatoxin; 7'C-(4-(4-((maleimido)methyl)

cyclohexanecarbonyl)piperazin-1-yl)-amatoxin; 7'C-(4-(6-(4-((maleimido)methyl)cyclohexanecarboxamido)hexanoyl)piperazin-1-yl)-amatoxin; 7'C-(4-(2-(6-(maleimido)hexanamido)ethyl)piperidin-1-yl)-amatoxin; 7'C-(4-(2-(6-(6-(maleimido)hexanamido)hexanamido)ethyl)piperidin-1-yl)-amatoxin; 7'C-(4-(2-(4-((maleimido)methyl)cyclohexanecarboxamido)ethyl)piperidin-1-yl)-amatoxin; 7'C-(4-(2-(6-(4-((maleimido)methyl)cyclohexanecarboxamido)hexanamido)ethyl)piperidin-1-yl)-amatoxin; 7'C-(4-(2-(3-carboxypropanamido)ethyl)piperidin-1-yl)-amatoxin; 7'C-(4-(2-(2-bromoacetamido)ethyl)piperidin-1-yl)-amatoxin; 7'C-(4-(2-(3-(pyridin-2-yldisulfanyl)propanamido)ethyl)piperidin-1-yl)-amatoxin; 7'C-(4-(2-(4-(maleimido)butanamido)ethyl)piperidin-1-yl)-amatoxin; 7'C-(4-(2-(maleimido)acetyl)piperazin-1-yl)-amatoxin; 7'C-(4-(3-(maleimido)propanoyl)piperazin-1-yl)-amatoxin; 7'C-(4-(4-(maleimido)butanoyl)piperazin-1-yl)-amatoxin; 7'C-(4-(2-(6-(4-((maleimido)methyl)cyclohexanecarboxamido)hexanamido)ethyl)piperidin-1-yl)-amatoxin; 7'C-(3-((6-(maleimido)hexanamido)methyl)pyrrolidin-1-yl)-amatoxin; 7'C-(3-((6-(6-(maleimido)hexanamido)hexanamido)methyl)pyrrolidin-1-yl)-amatoxin; 7'C-(3-((4-((maleimido)methyl)cyclohexanecarboxamido)methyl)pyrrolidin-1-yl)-amatoxin; 7'C-(3-((6-((4-(maleimido)methyl)cyclohexanecarboxamido)hexanamido)methyl)pyrrolidin-1-yl)-amatoxin; 7'C-(4-(2-(6-(2-(aminooxy)acetamido)hexanamido)ethyl)piperidin-1-yl)-amatoxin; 7'C-(4-(2-(4-(2-(aminooxy)acetamido)butanamido)ethyl)piperidin-1-yl)-amatoxin; 7'C-(4-(4-(2-(aminooxy)acetamido)butanoyl)piperazin-1-yl)-amatoxin; 7'C-(4-(6-(2-(aminooxy)acetamido)hexanoyl)piperazin-1-yl)-amatoxin; 7'C-((4-(6-(maleimido)hexanamido)piperidin-1-yl)methyl)-amatoxin; 7'C-((4-(2-(6-(maleimido)hexanamido)ethyl)piperidin-1-yl)methyl)-amatoxin; 7'C-((4-(6-(maleimido)hexanoyl)piperazin-1-yl)methyl)-amatoxin; (R)-7'C-((3-((6-(maleimido)hexanamido)methyl)pyrrolidin-1-yl)methyl)-amatoxin; (S)-7'C-((3-((6-(maleimido)hexanamido)methyl)pyrrolidin-1-yl)methyl)-amatoxin; 7'C-((4-(2-(6-(6-(maleimido)hexanamido)hexanamido)ethyl)piperidin-1-yl)methyl)-amatoxin; 7'C-((4-(2-(4-((maleimido)methyl)cyclohexanecarboxamido)ethyl)piperidin-1-yl)methyl)-amatoxin; 7'C-((4-(2-(6-(4-((maleimido)methyl)cyclohexanecarboxamido)hexanamido)ethyl)piperidin-1-yl)methyl)-amatoxin; 7'C-((4-(2-(6-(maleimido)hexanamido)ethyl)piperazin-1-yl)methyl)-amatoxin; 7'C-((4-(2-(6-(6-(maleimido)hexanamido)hexanamido)ethyl)piperazin-1-yl)methyl)-amatoxin; 7'C-((4-(2-(4-((maleimido)methyl)cyclohexanecarboxamido)ethyl)piperazin-1-yl)methyl)-amatoxin; 7'C-((4-(2-(6-(4-((maleimido)methyl)cyclohexanecarboxamido)hexanamido)ethyl)piperazin-1-yl)methyl)-amatoxin; 7'C-((3-((6-(6-(maleimido)hexanamido)hexanamido)-S-methyl)pyrrolidin-1-yl)methyl)-amatoxin; 7'C-((3-((6-(6-(maleimido)hexanamido)hexanamido)-R-methyl)pyrrolidin-1-yl)methyl)-amatoxin; 7'C-((3-((4-((maleimido)methyl)cyclohexanecarboxamido)-S-methyl)pyrrolidin-1-yl)methyl)-amatoxin; 7'C-((3-((4-((maleimido)methyl)cyclohexanecarboxamido)-R-methyl)pyrrolidin-1-yl)methyl)-amatoxin; 7'C-((3-((6-(4-((maleimido)methyl)cyclohexanecarboxamido)hexanamido)methyl)pyrrolidin-1-yl)methyl)-amatoxin; 7'C-((4-(2-(3-carboxypropanamido)ethyl)piperazin-1-yl)methyl)-amatoxin; 7'C-((4-(6-(6-(maleimido)hexanamido)hexanoyl)piperazin-1-yl)methyl)-amatoxin; 7'C-((4-(6-(4-((maleimido)methyl)cyclohexanecarboxamido)hexanoyl)piperazin-1-yl)methyl)-amatoxin; 7'C-((4-(2-(maleimido)acetyl)piperazin-1-yl)methyl)-amatoxin; 7'C-((4-(3-(maleimido)propanoyl)piperazin-1-yl)methyl)-amatoxin; 7'C-((4-(4-(maleimido)butanoyl)piperazin-1-yl)methyl)-amatoxin; 7'C-(4-(2-(2-(maleimido)acetamido)ethyl)piperidin-1-yl)methyl)-amatoxin; 7'C-((4-(2-(4-(maleimido)butanamido)ethyl)piperidin-1-yl)methyl)-amatoxin; 7'C-((4-(2-(6-(4 ((maleimido)methyl)cyclohexanecarboxamido)hexanamido)ethyl)piperidin-1-yl)methyl)-amatoxin; 7'C-((3-((6-(maleimido)hexanamido)methyl)azetidin-1-yl)methyl)-amatoxin; 7'C-((3-(2-(6-(maleimido)hexanamido)ethyl)azetidin-1-yl)methyl)-amatoxin; 7'C-((3-((4-((maleimido)methyl)cyclohexanecarboxamido)methyl)azetidin-1-yl)methyl)-amatoxin; 7'C-((3-(2-(4-((maleimido)methyl)cyclohexanecarboxamido)ethyl)azetidin-1 yl)methyl)-amatoxin; 7'C-((3-(2-(6-(4-((maleimido)methyl)cyclohexanecarboxamido)hexanamido)ethyl)azetidin-1-yl)methyl)-amatoxin; 7'C-(((2-(6-(maleimido)-N-methyl hexanamido)ethyl)(methyl)amino)methyl)-amatoxin; 7'C-(((4-(6-(maleimido)-N-methyl hexanamido)butyl(methyl)amino)methyl)-amatoxin; 7'C-((2-(2-(6-(maleimido)hexanamido)ethyl)aziridin-1-yl)methyl)-amatoxin; 7'C-((2-(2-(6-(4-((maleimido)methyl)cyclohexanecarboxamido)hexanamido)ethyl)aziridin-1-yl)methyl)-amatoxin; 7'C-((4-(6-(6-(2-(aminooxy)acetamido)hexanamido)hexanoyl)piperazin-1-yl)methyl)-amatoxin; 7'C-((4-(1-(aminooxy)-2-oxo-6,9,12,15-tetraoxa-3-azaheptadecan-17-oyl)piperazin-1-yl)methyl)-amatoxin; 7'C-((4-(2-(2-(aminooxy)acetamido)acetyl)piperazin-1-yl)methyl)-amatoxin; 7'C-((4-(3-(2-(aminooxy)acetamido)propanoyl)piperazin-1-yl)methyl)-amatoxin; 7'C-((4-(4-(2-(aminooxy)acetamido)butanoyl)piperazin-1-yl)methyl)-amatoxin; 7'C-((4-(2-(6-(2-(aminooxy)acetamido)hexanamido)ethyl)piperidin-1-yl)methyl)-amatoxin; 7'C-((4-(2-(2-(2-(aminooxy)acetamido)acetamido)ethyl)piperidin-1-yl)methyl)-amatoxin; 7'C-((4-(2-(4-(2-(aminooxy)acetamido)butanamido)ethyl)piperidin-1-yl)methyl)-amatoxin; 7'C-((4-(20-(aminooxy)-4,19-dioxo-6,9,12,15-tetraoxa-3,18-diazaicosyl)piperidin-1-yl)methyl)-amatoxin; 7'C-(((2-(6-(2-(aminooxy)acetamido)-N-methylhexanamido)ethyl)(methyl)amino)methyl)-amatoxin; 7'C-(((4-(6-(2-(aminooxy)acetamido)-N-methylhexanamido)butyl)(methyl)amino)methyl)-amatoxin; 7'C-((3-((6-(4-((maleimido)methyl)cyclohexanecarboxamido)hexanamido)methyl)pyrrolidin-1-yl)-S-methyl)-amatoxin; 7'C-((3-((6-(4-((maleimido)methyl)cyclohexanecarboxamido)hexanamido)-R-methyl)pyrrolidin-1-yl)methyl)-amatoxin; 7'C-((4-(2-(2-bromoacetamido)ethyl)piperazin-1-yl)methyl)-amatoxin; 7'C-((4-(2-(2-bromoacetamido)ethyl)piperidin-1-yl)methyl)-amatoxin; 7'C-((4-(2-(3-(pyridine-2-yldisulfanyl)propanamido)ethyl)piperidin-1-yl)methyl)-amatoxin; 6'O-(6-(6-(maleimido)hexanamido)hexyl)-amatoxin; 6'O-(5-(4-((maleimido)methyl)cyclohexanecarboxamido)pentyl)-amatoxin; 6'O-(2-((6-(maleimido)hexyl)oxy)-2-oxoethyl)-amatoxin; 6'O-((6-(maleimido)hexyl)carbamoyl)-amatoxin; 6'O-((6-(4-((maleimido)methyl)cyclohexanecarboxamido)hexyl)carbamoyl)-amatoxin; 6'O-(6-(2-bromoacetamido)hexyl)-amatoxin; 7'C-(4-(6-(azido)hexanamido)piperidin-1-yl)-amatoxin; 7'C-(4-(hex-5-ynoylamino)piperidin-1-yl)-amatoxin; 7'C-(4-(2-(6-(maleimido)hexanamido)ethyl)piperazin-1-yl)-amatoxin; 7'C-(4-(2-(6-(6-(maleimido)hexanamido)hexanamido)ethyl)piperazin-1-yl)-amatoxin; 6'O-(6-(6-(11,12-didehydro-5,6-dihydro-dibenz[b,f]azocin-5-yl)-6-oxohexanamido)hexyl)-amatoxin; 6'O-(6-(hex-5-ynoylamino)hexyl)-amatoxin; 6'O-(6-(2-(aminooxy)acetylamido)hexyl)-amatoxin; 6'O-((6-aminooxy)hexyl)-amatoxin; and 6'O-(6-(2-iodoacetamido)hexyl)-amatoxin. The foregoing linkers, among others useful in conjunction with the compositions and methods described herein, are described, for example, in US Patent Application Publication No. 2015/0218220, the disclosure of which is incorporated herein by reference in its entirety.

Additional cytotoxins that can be conjugated to antibodies, antigen-binding fragments thereof, and ligands that recognize and bind CD117 (such as GNNK+CD117 for use in directly treating a cancer, autommine condition, or for conditioning a patient (e.g., a human patient) in preparation for hematopoietic stem cell transplant therapy include, without limitation, 5-ethynyluracil, abiraterone, acylfulvene, adecypenol, adozelesin, aldesleukin, altretamine, ambamustine, amidox, amifostine, aminolevulinic acid, amrubicin, amsacrine, anagrelide, anastrozole, andrographolide, angiogenesis inhibitors, antarelix, anti-dorsalizing morphogenetic protein-1, antiandrogen, prostatic carcinoma, antiestrogen, antineoplaston, antisense oligonucleotides, aphidicolin glycinate, apoptosis gene modulators, apoptosis regulators, apurinic acid, asulacrine, atamestane, atrimustine, axinastatin 1, axinastatin 2, axinastatin 3, azasetron, azatoxin, azatyrosine, baccatin III derivatives, balanol, batimastat, BCR/ABL antagonists, benzochlorins, benzoylstaurosporine, beta lactam derivatives, beta-alethine, betaclamycin B, betulinic acid, bFGF inhibitors, bicalutamide, bisantrene, bisaziridinylspermine, bisnafide, bistratene A, bizelesin, breflate, bleomycin A2, bleomycin B2, bropirimine, budotitane, buthionine sulfoximine, calcipotriol, calphostin C, camptothecin derivatives (e.g., 10-hydroxy-camptothecin), capecitabine, carboxamide-amino-triazole, carboxyamidotriazole, carzelesin, casein kinase inhibitors, castanospermine, cecropin B, cetrorelix, chlorins, chloroquinoxaline sulfonamide, cicaprost, cis-porphyrin, cladribine, clomifene and analogues thereof, clotrimazole, collismycin A, collismycin B, combretastatin A4, combretastatin analogues, conagenin, crambescidin 816, crisnatol, cryptophycin 8, cryptophycin A derivatives, curacin A, cyclopentanthraquinones, cycloplatam, cypemycin, cytarabine ocfosfate, cytolytic factor, cytostatin, dacliximab, decitabine, dehydrodidemnin B, 2'deoxycoformycin (DCF), deslorelin, dexifosfamide, dexrazoxane, dexverapamil, diaziquone, didemnin B, didox, diethylnorspermine, dihydro-5-azacytidine, dihydrotaxol, dioxamycin, diphenyl spiromustine, discodermolide, docosanol, dolasetron, doxifluridine, droloxifene, dronabinol, duocarmycin SA, ebselen, ecomustine, edelfosine, edrecolomab, eflornithine, elemene, emitefur, epothilones, epithilones, epristeride, estramustine and analogues thereof, etoposide, etoposide 4'-phosphate (also referred to as etopofos), exemestane, fadrozole, fazarabine, fenretinide, filgrastim, finasteride, flavopiridol, flezelastine, fluasterone, fludarabine, fluorodaunorunicin hydrochloride, forfenimex, formestane, fostriecin, fotemustine, gadolinium texaphyrin, gallium nitrate, galocitabine, ganirelix, gelatinase inhibitors, gemcitabine, glutathione inhibitors, hepsulfam, homoharringtonine (HHT), hypericin, ibandronic acid, idoxifene, idramantone, ilmofosine, ilomastat, imidazoacridones, imiquimod, immunostimulant peptides, iobenguane, iododoxorubicin, ipomeanol, irinotecan, iroplact, irsogladine, isobengazole, jasplakinolide, kahalalide F, lamellarin-N triacetate, lanreotide, leinamycin, lenograstim, lentinan sulfate, leptolstatin, letrozole, lipophilic platinum compounds, lissoclinamide 7, lobaplatin, lometrexol, lonidamine, losoxantrone, loxoribine, lurtotecan, lutetium texaphyrin, lysofylline, masoprocol, maspin, matrix metalloproteinase inhibitors, menogaril, rnerbarone, meterelin, methioninase, metoclopramide, MIF inhibitor, ifepristone, miltefosine, mirimostim, mithracin, mitoguazone, mitolactol, mitomycin and analogues thereof, mitonafide, mitoxantrone, mofarotene, molgramostim, mycaperoxide B, myriaporone, N-acetyldinaline, N-substituted benzamides, nafarelin, nagrestip, napavin, naphterpin, nartograstim, nedaplatin, nemorubicin, neridronic acid, nilutamide, nisamycin, nitrullyn, octreotide, okicenone, onapristone, ondansetron, oracin, ormaplatin, oxaliplatin, oxaunomycin, paclitaxel and analogues thereof, palauamine, palmitoylrhizoxin, pamidronic acid, panaxytriol, panomifene, parabactin, pazelliptine, pegaspargase, peldesine, pentosan polysulfate sodium, pentostatin, pentrozole, perflubron, perfosfamide, phenazinomycin, picibanil, pirarubicin, piritrexim, podophyllotoxin, porfiromycin, purine nucleoside phosphorylase inhibitors, raltitrexed, rhizoxin, rogletimide, rohitukine, rubiginone B1, ruboxyl, safingol, saintopin, sarcophytol A, sargramostim, sobuzoxane, sonermin, sparfosic acid, spicamycin D, spiromustine, stipiamide, sulfinosine, tallimustine, tegafur, temozolomide, teniposide, thaliblastine, thiocoraline, tirapazamine, topotecan, topsentin, triciribine, trimetrexate, veramine, vinorelbine, vinxaltine, vorozole, zeniplatin, and zilascorb, among others.

Linkers for Chemical Conjugation

A variety of linkers can be used to conjugate antibodies, antigen-binding fragments, and ligands described herein (e.g., antibodies, antigen-binding fragments thereof, and ligands that recognize and bind CD117 (such as GNNK+CD117) with a cytotoxic molecule. Linkers include those that may be cleaved, for instance, by enzymatic hydrolysis, photolysis, hydrolysis under acidic conditions, hydrolysis under basic conditions, oxidation, disulfide reduction, nucleophilic cleavage, or organometallic cleavage (see, for example, Leriche et al., Bioorg. Med. Chem., 20:571-582, 2012, the disclosure of which is incorporated herein by reference as it pertains to linkers suitable for covalent conjugation). Examples of linkers useful for the synthesis of drug-antibody conjugates and drug-ligand conjugates include those that contain electrophiles, such as Michael acceptors (e.g., maleimides), activated esters, electron-deficient carbonyl compounds, and aldehydes, among others, suitable for reaction with nucleophilic substituents present within antibodies or antigen-binding fragments, such as amine and thiol moieties. For instance, linkers suitable for the synthesis of drug-antibody conjugates and drug-ligand conjugates include, without limitation, succinimidyl 4-(N-maleimidomethyl)-cyclohexane-L-carboxylate (SMCC), N-succinimidyl iodoacetate (SIA), sulfo-SMCC, m-maleimidobenzoyl-N-hydroxysuccinimidyl ester (MBS), sulfo-MBS, and succinimidyl iodoacetate, among others described, for instance, Liu et al., 18:690-697, 1979, the disclosure of which is incorporated herein by reference as it pertains to linkers for chemical conjugation. Additional linkers include the non-cleavable maleimidocaproyl linkers, which are particularly useful for the conjugation of microtubule-disrupting agents such as auristatins, are described by Doronina et al., Bioconjugate Chem. 17:14-24, 2006, the disclosure of which is incorporated herein by reference as it pertains to linkers for chemical conjugation. Additional linkers suitable for the synthesis of drug-antibody conjugates and drug-ligand conjugates as described herein include those capable of releasing a cytotoxin by a 1,6-elimination process, such as p-aminobenzyl alcohol (PABC), 6-maleimidohexanoic acid, pH-sensitive carbonates, and other reagents described in Jain et al., Pharm. Res. 32:3526-3540, 2015, the disclosure of which is incorporated herein by reference in its entirety.

Linkers that can be used to conjugate an antibody, antigen-binding fragment thereof, or ligand to a cytotoxic agent include those that are covalently bound to the cytotoxic agent on one end of the linker and, on the other end of the linker, contain a chemical moiety formed from a coupling reaction between a reactive substituent present on the linker and a reactive substituent present within the antibody, antigen-binding fragment thereof, or ligand that binds CD117 (such as GNNK+CD117). Reactive substituents that may be present within an antibody, antigen-binding fragment thereof, or ligand that binds CD117 (such as GNNK+ CD117) include, without limitation, hydroxyl moieties of serine, threonine, and tyrosine residues; amino moieties of lysine residues; carboxyl moieties of aspartic acid and glutamic acid residues; and thiol moieties of cysteine residues, as well as propargyl, azido, haloaryl (e.g., fluoroaryl), haloheteroaryl (e.g., fluoroheteroaryl), haloalkyl, and haloheteroalkyl moieties of non-naturally occurring amino acids. Linkers useful in conjunction with the antibody-drug and ligand-drug conjugates described herein include, without limitation, linkers containing chemical moieties formed by coupling reactions as depicted in Table 1, below. Curved lines designate points of attachment to the antibody, antigen-binding fragment, or ligand and the cytotoxic molecule, respectively.

TABLE 1

Exemplary chemical moieties formed by coupling reactions in the formation of antibody-drug and ligand-drug conjugates

| Exemplary Coupling Reactions | Chemical Moiety Formed by Coupling Reactions |
|---|---|
| [3 + 2] Cycloaddition | 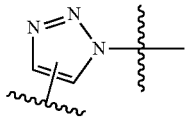 |
| [3 + 2] Cycloaddition | 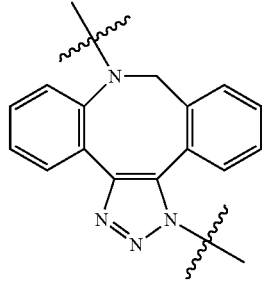 [SMILES: *N1Cc2ccccc2-c2c(nnn2*)-c2ccccc21] |
| [3 + 2] Cycloaddition, Esterification | 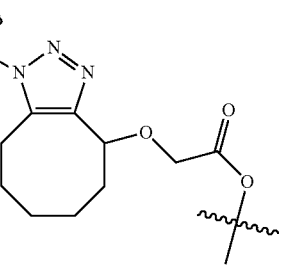 |
| [3 + 2] Cycloaddition, Esterification | 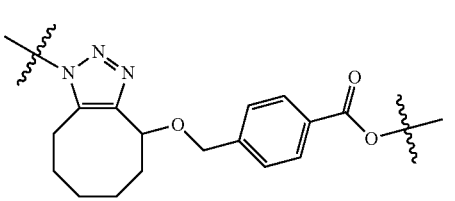 [SMILES: *OC(=O)c1ccc(COC2CCCCCc3c2nnn3*)cc1] |
| [3 + 2] Cycloaddition, Esterification | 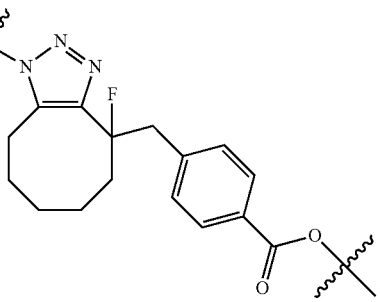 |
| [3 + 2] Cycloaddition, Esterification | 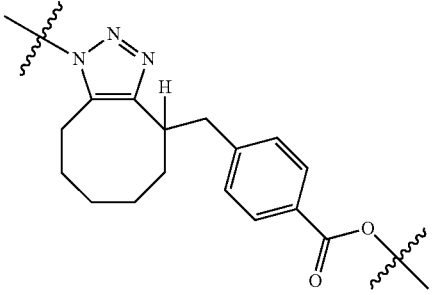 [SMILES: *OC(=O)c1ccc(CC2(F)CCCCCc3c2nnn3*)cc1] |
| [3 + 2] Cycloaddition, Esterification | 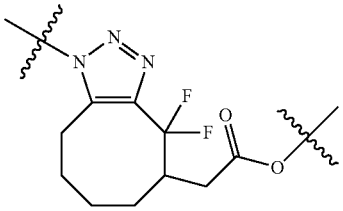 [SMILES: *OC(=O)CC1CCCCc2c(nnn2*)C1(F)F] |
| [3 + 2] Cycloaddition, Esterification | 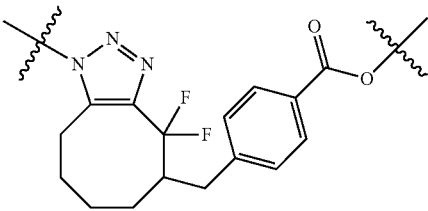 [SMILES: *OC(=O)c1ccc(CC2CCCCc3c(nnn3*)C2(F)F)cc1] |
| [3 + 2] Cycloaddition, Esterification | 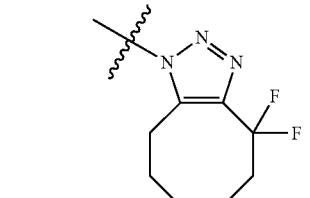 |
| [3 + 2] Cycloaddition, Esterification | 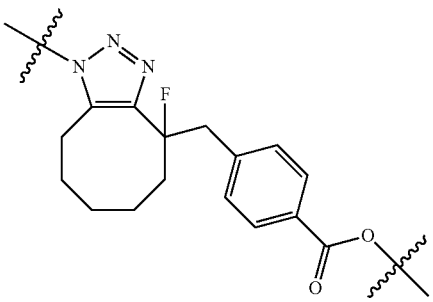 |

TABLE 1-continued

Exemplary chemical moieties formed by coupling reactions in the formation of antibody-drug and ligand-drug conjugates

| Exemplary Coupling Reactions | Chemical Moiety Formed by Coupling Reactions |
|---|---|
| [3 + 2] Cycloaddition, Esterification | |
| [3 + 2] Cycloaddition, Esterification | |
| [3 + 2] Cycloaddition, Esterification | |
| [3 + 2] Cycloaddition, Esterification | |
| [3 + 2] Cycloaddition, Etherification | |
| [3 + 2] Cycloaddition | |
| Michael addition | |
| Michael addition | |
| Imine condensation, Amidation | |
| Imine condensation | |
| Disulfide formation | |
| Thiol alkylation | |

TABLE 1-continued

Exemplary chemical moieties formed by coupling reactions in the formation of antibody-drug and ligand-drug conjugates

| Exemplary Coupling Reactions | Chemical Moiety Formed by Coupling Reactions |
|---|---|
| Condensation, Michael addition | (structure showing NH, N-H, S linkage to a succinimide with two C=O groups) |

Methods of Treatment

As described herein, hematopoietic stem cell transplant therapy can be administered to a subject in need of treatment so as to populate or re-populate one or more blood cell types. Hematopoietic stem cells generally exhibit multi-potency, and can thus differentiate into multiple different blood lineages including, but not limited to, granulocytes (e.g., promyelocytes, neutrophils, eosinophils, basophils), erythrocytes (e.g., reticulocytes, erythrocytes), thrombocytes (e.g., megakaryoblasts, platelet producing megakaryocytes, platelets), monocytes (e.g., monocytes, macrophages), dendritic cells, microglia, osteoclasts, and lymphocytes (e.g., NK cells, B-cells and T-cells). Hematopoietic stem cells are additionally capable of self-renewal, and can thus give rise to daughter cells that have equivalent potential as the mother cell, and also feature the capacity to be reintroduced into a transplant recipient whereupon they home to the hematopoietic stem cell niche and re-establish productive and sustained hematopoiesis.

Hematopoietic stem cells can thus be administered to a patient defective or deficient in one or more cell types of the hematopoietic lineage in order to re-constitute the defective or deficient population of cells in vivo, thereby treating the pathology associated with the defect or depletion in the endogenous blood cell population. The compositions and methods described herein can thus be used to treat a non-malignant hemoglobinopathy (e.g., a hemoglobinopathy selected from the group consisting of sickle cell anemia, thalassemia, Fanconi anemia, aplastic anemia, and Wiskott-Aldrich syndrome). Additionally or alternatively, the compositions and methods described herein can be used to treat an immunodeficiency, such as a congenital immunodeficiency. Additionally or alternatively, the compositions and methods described herein can be used to treat an acquired immunodeficiency (e.g., an acquired immunodeficiency selected from the group consisting of HIV and AIDS). The compositions and methods described herein can be used to treat a metabolic disorder (e.g., a metabolic disorder selected from the group consisting of glycogen storage diseases, mucopolysaccharidoses, Gaucher's Disease, Hurlers Disease, sphingolipidoses, and metachromatic leukodystrophy).

Additionally or alternatively, the compositions and methods described herein can be used to treat a malignancy or proliferative disorder, such as a hematologic cancer, myeloproliferative disease. In the case of cancer treatment, the compositions and methods described herein may be administered to a patient so as to deplete a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during cancer cell eradication, such as during systemic chemotherapy. Exemplary hematological cancers that can be treated using the compositions and methods described herein include, without limitation, acute myeloid leukemia, acute lymphoid leukemia, chronic myeloid leukemia, chronic lymphoid leukemia, multiple myeloma, diffuse large B-cell lymphoma, and non-Hodgkin's lymphoma, as well as other cancerous conditions, including neuroblastoma.

Additional diseases that can be treated with the compositions and methods described herein include, without limitation, adenosine deaminase deficiency and severe combined immunodeficiency, hyper immunoglobulin M syndrome, Chediak-Higashi disease, hereditary lymphohistiocytosis, osteopetrosis, osteogenesis imperfecta, storage diseases, thalassemia major, systemic sclerosis, systemic lupus erythematosus, multiple sclerosis, and juvenile rheumatoid arthritis.

The antibodies, antigen-binding fragments thereof, ligands, and conjugates described herein may be used to induce solid organ transplant tolerance. For instance, the compositions and methods described herein may be used to deplete or ablate a population of cells from a target tissue (e.g., to deplete hematopoietic stem cells from the bone marrow stem cell niche). Following such depletion of cells from the target tissues, a population of stem or progenitor cells from an organ donor (e.g., hematopoietic stem cells from the organ donor) may be administered to the transplant recipient, and following the engraftment of such stem or progenitor cells, a temporary or stable mixed chimerism may be achieved, thereby enabling long-term transplant organ tolerance without the need for further immunosuppressive agents. For example, the compositions and methods described herein may be used to induce transplant tolerance in a solid organ transplant recipient (e.g., a kidney transplant, lung transplant, liver transplant, and heart transplant, among others). The compositions and methods described herein are well-suited for use in connection the induction of solid organ transplant tolerance, for instance, because a low percentage temporary or stable donor engraftment is sufficient to induce long-term tolerance of the transplanted organ.

In addition, the compositions and methods described herein can be used to treat cancers directly, such as cancers characterized by cells that are CD117+. For instance, the compositions and methods described herein can be used to treat leukemia, particularly in patients that exhibit CD117+ leukemic cells. By depleting CD117+ cancerous cells, such as leukemic cells, the compositions and methods described herein can be used to treat various cancers directly. Exemplary cancers that may be treated in this fashion include hematological cancers, such as acute myeloid leukemia, acute lymphoid leukemia, chronic myeloid leukemia, chronic lymphoid leukemia, multiple myeloma, diffuse large B-cell lymphoma, and non-Hodgkin's lymphoma, In addition, the compositions and methods described herein can be used to treat autoimmune disorders. For instance, an antibody, antigen-binding fragment thereof, or ligand can be administered to a subject, such as a human patient suffering from an autoimmune disorder, so as to kill a CD117+ immune cell. The CD117+ immune cell may be an autoreactive lymphocyte, such as a T-cell that expresses a T-cell receptor that specifically binds, and mounts an immune response against, a self antigen. By depleting self-reactive, CD117+ cells, the compositions and methods described herein can be used to treat autoimmune pathologies, such as those described below. Additionally or alternatively, the compositions and methods described herein can be used to treat an autoimmune disease by depleting a population of endogenous hematopoietic stem cells prior to hematopoietic stem cell transplantation therapy, in which case the transplanted cells can home to a niche created by the endogenous cell depletion step and establish productive hematopoiesis. This, in turn, can re-constitute a population of cells depleted during autoimmune cell eradication.

Autoimmune diseases that can be treated using the compositions and methods described herein include, without limitation, psoriasis, psoriatic arthritis, Type 1 diabetes mellitus (Type 1 diabetes), rheumatoid arthritis (RA), human systemic lupus (SLE), multiple sclerosis (MS), inflammatory bowel disease (IBD), lymphocytic colitis, acute disseminated encephalomyelitis (ADEM), Addison's disease, alopecia universalis, ankylosing spondylitisis, antiphospholipid antibody syndrome (APS), aplastic anemia, autoimmune hemolytic anemia, autoimmune hepatitis, autoimmune inner ear disease (AIED), autoimmune lymphoproliferative syndrome (ALPS), autoimmune oophoritis, Balo disease, Behcet's disease, bullous pemphigoid, cardiomyopathy, Chagas' disease, chronic fatigue immune dysfunction syndrome (CFIDS), chronic inflammatory demyelinating polyneuropathy, Crohn's disease, cicatrical pemphigoid, coeliac sprue-dermatitis herpetiformis, cold agglutinin disease, CREST syndrome, Degos disease, discoid lupus, dysautonomia, endometriosis, essential mixed cryoglobulinemia, fibromyalgia-fibromyositis, Goodpasture's syndrome, Grave's disease, Guillain-Barre syndrome (GBS), Hashimoto's thyroiditis, Hidradenitis suppurativa, idiopathic and/or acute thrombocytopenic purpura, idiopathic pulmonary fibrosis, IgA neuropathy, interstitial cystitis, juvenile arthritis, Kawasaki's disease, lichen planus, Lyme disease, Meniere disease, mixed connective tissue disease (MCTD), myasthenia gravis, neuromyotonia, opsoclonus myoclonus syndrome (OMS), optic neuritis, Ord's thyroiditis, pemphigus vulgaris, pernicious anemia, polychondritis, polymyositis and dermatomyositis, primary biliary cirrhosis, polyarteritis nodosa, polyglandular syndromes, polymyalgia rheumatica, primary agammaglobulinemia, Raynaud phenomenon, Reiter's syndrome, rheumatic fever, sarcoidosis, scleroderma, Sjögren's syndrome, stiff person syndrome, Takayasu's arteritis, temporal arteritis (also known as "giant cell arteritis"), ulcerative colitis, collagenous colitis, uveitis, vasculitis, vitiligo, vulvodynia ("vulvar vestibulitis"), and Wegener's granulomatosis.

Routes of Administration and Dosing

Antibodies, antigen-binding fragments thereof, and ligands described herein can be administered to a patient (e.g., a human patient suffering from cancer, an autoimmune disease, or in need of hematopoietic stem cell transplant therapy) in a variety of dosage forms. For instance, antibodies, antigen-binding fragments thereof, and ligands described herein can be administered to a patient suffering from cancer, an autoimmune disease, or in need of hematopoietic stem cell transplant therapy in the form of an aqueous solution, such as an aqueous solution containing one or more pharmaceutically acceptable excipients. Pharmaceutically acceptable excipients for use with the compositions and methods described herein include viscosity-modifying agents. The aqueous solution may be sterilized using techniques known in the art.

The antibodies, antigen-binding fragments, and ligands described herein may be administered by a variety of routes, such as orally, transdermally, subcutaneously, intranasally, intravenously, intramuscularly, intraocularly, or parenterally. The most suitable route for administration in any given case will depend on the particular antibody, antigen-binding fragment, or ligand administered, the patient, pharmaceutical formulation methods, administration methods (e.g., administration time and administration route), the patient's age, body weight, sex, severity of the diseases being treated, the patient's diet, and the patient's excretion rate.

The effective dose of an antibody, antigen-binding fragment thereof, or ligand described herein can range, for example from about 0.001 to about 100 mg/kg of body weight per single (e.g., bolus) administration, multiple administrations, or continuous administration, or to achieve an optimal serum concentration (e.g., a serum concentration of 0.0001-5000 µg/mL) of the antibody, antigen-binding fragment thereof, or ligand. The dose may be administered one or more times (e.g., 2-10 times) per day, week, or month to a subject (e.g., a human) suffering from cancer, an autoimmune disease, or undergoing conditioning therapy in preparation for receipt of a hematopoietic stem cell transplant. In the case of a conditioning procedure prior to hematopoietic stem cell transplantation, the antibody, antigen-binding fragment thereof, or ligand can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

EXAMPLES

The following examples are put forth so as to provide those of ordinary skill in the art with a description of how the compositions and methods described herein may be used, made, and evaluated, and are intended to be purely exemplary of the invention and are not intended to limit the scope of what the inventors regard as their invention.

Example 1. Administration of an Anti-CD117 Antibody to a Human Patient in Preparation for Hematopoietic Stem Cell Transplant Therapy Using the methods disclosed herein, a physician of skill in the art can administer to a human patient in need of hematopoietic stem cell transplant therapy an antibody or antigen-binding fragment thereof capable of binding an antigen expressed by hematopoietic stem cells, such as an antibody or antigen-biding fragment thereof that binds CD117 (for example, an antibody or antigen-binding fragment thereof that binds GNNK+CD117). In this fashion, a population of endogenous hematopoietic stem cells can be depleted prior to administration of an exogenous hematopoietic stem cell graft so as to promote engraftment of the hematopoietic stem cell graft. The antibody may be covalently conjugated to a toxin, such as a cytotoxic molecule described herein or known in the art. For instance, an anti-CD117 antibody or antigen-binding fragment thereof (such as an anti-GNNK+CD117 antibody or antigen-binding fragment thereof) can be covalently conjugated to a cytotoxin, such as pseudomonas exotoxin A, deBouganin, diphtheria toxin, an amatoxin, such as α-amanitin, saporin, maytansine, a maytansinoid, an auristatin, an anthracycline, a calicheamicin, irinotecan, SN-38, a duocarmycin, a pyrrolobenzodiazepine, a pyrrolobenzodiazepine dimer, an indolinobenzodiazepine, an indolinobenzodiazepine dimer, or a variant thereof. This conjugation can be performed using covalent bond-forming techniques described herein or known in the art. The antibody, antigen-binding fragment thereof, or drug-antibody conjugate can subsequently be administered to the patient, for example, by intravenous administration, prior to transplantation of exogenous hematopoietic stem cells (such as autologous, syngeneic, or allogeneic hematopoietic stem cells) to the patient.

The anti-CD117 (e.g., anti-GNNK+CD117) antibody, antigen-binding fragment thereof, or drug-antibody conjugate can be administered in an amount sufficient to reduce the quantity of endogenous hematopoietic stem cells, for example, by 10%, 20%, 30%, 40%, 50%, 60%, 70%, 80%, 90%, 95%, or more prior to hematopoietic stem cell transplant therapy. The reduction in hematopoietic stem cell count can be monitored using conventional techniques known in the art, such as by FACS analysis of cells expressing characteristic hematopoietic stem cell surface antigens in a blood sample withdrawn from the patient at varying intervals during conditioning therapy. For instance, a physician of skill in the art can withdraw a blood sample from the patient at various time points during conditioning therapy and determine the extent of endogenous hematopoietic stem cell reduction by conducting a FACS analysis to elucidate the relative concentrations of hematopoietic stem cells in the sample using antibodies that bind to hematopoietic stem cell marker antigens. According to some embodiments, when the concentration of hematopoietic stem cells has reached a minimum value in response to conditioning therapy with an anti-CD117 (e.g., anti-GNNK+CD117) antibody, antigen-binding fragment thereof, or drug-antibody conjugate, the physician may conclude the conditioning therapy, and may begin preparing the patient for hematopoietic stem cell transplant therapy.

The anti-CD117 (e.g., anti-GNNK+CD117) antibody, antigen-binding fragment thereof, or drug-antibody conjugate can be administered to the patient in an aqueous solution containing one or more pharmaceutically acceptable excipients, such as a viscosity-modifying agent. The aqueous solution may be sterilized using techniques described herein or known in the art. The antibody, antigen-binding fragment thereof, or drug-antibody conjugate can be administered to the patient at a dosage of, for example, from 0.001 mg/kg to 100 mg/kg prior to administration of a hematopoietic stem cell graft to the patient. The antibody, antigen-binding fragment thereof, or drug-antibody conjugate can be administered to the patient at a time that optimally promotes engraftment of the exogenous hematopoietic stem cells, for instance, from 1 hour to 1 week (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, or 7 days) or more prior to administration of the exogenous hematopoietic stem cell transplant.

Following the conclusion of conditioning therapy, the patient may then receive an infusion (e.g., an intravenous infusion) of exogenous hematopoietic stem cells, such as from the same physician that performed the conditioning therapy or from a different physician. The physician may administer the patient an infusion of autologous, syngeneic, or allogeneic hematopoietic stem cells, for instance, at a dosage of from $1 \times 10^3$ to $1 \times 10^9$ hematopoietic stem cells/kg. The physician may monitor the engraftment of the hematopoietic stem cell transplant, for example, by withdrawing a blood sample from the patient and determining the increase in concentration of hematopoietic stem cells or cells of the hematopoietic lineage (such as megakaryocytes, thrombocytes, platelets, erythrocytes, mast cells, myeoblasts, basophils, neutrophils, eosinophils, microglia, granulocytes, monocytes, osteoclasts, antigen-presenting cells, macrophages, dendritic cells, natural killer cells, T-lymphocytes, and B-lymphocytes) following administration of the transplant. This analysis may be conducted, for example, from 1 hour to 6 months, or more, following hematopoietic stem cell transplant therapy (e.g., 1 hour, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 2 days, 3 days, 4 days, 5 days, 6 days, 7 days, 2 weeks, 3 weeks, 4 weeks, 5 weeks, 6 weeks, 7 weeks, 8 weeks, 9 weeks, 10 weeks, 11 weeks, 12 weeks, 13 weeks, 14 weeks, 15 weeks, 16 weeks, 17 weeks, 18 weeks, 19 weeks, 20 weeks, 21 weeks, 22 weeks, 23 weeks, 24 weeks, or more). A finding that the concentration of hematopoietic stem cells or cells of the hematopoietic lineage has increased (e.g., by 1%, 2%, 3%, 4%, 5%, 6%, 7%, 8%, 9%, 10%, 20%, 30%, 40%, 50%, 60%, 70%, 80%, 90%, 100%, 200%, 500%, or more) following the transplant therapy relative to the concentration of the corresponding cell type prior to transplant therapy provides one indication that treatment with the anti-CD117 (e.g., anti-GNNK+ CD117) antibody, antigen-binding fragment thereof, or drug-antibody conjugate has successfully promoted engraftment of the transplanted hematopoietic stem cell graft.

Example 2. Generating Antibodies Capable of Binding Hematopoietic Stem Cells by Phage Display An exemplary method for in vitro evolution of anti-CD117 (e.g., anti-GNNK+CD117) antibodies for use with the compositions and methods described herein is phage display. Phage display libraries can be created by making a designed series of mutations or variations within a coding sequence for the CDRs of an antibody or the analogous regions of an antibody-like scaffold (e.g., the BC, CD, and DE loops of $^{10}$Fn3 domains).

The template antibody-encoding sequence into which these mutations are introduced may be, for example, a naive human germline sequence. These mutations can be performed using standard mutagenesis techniques known in the art. Each mutant sequence thus encodes an antibody corresponding to the template save for one or more amino acid variations. Retroviral and phage display vectors can be engineered using standard vector construction techniques known in the art. P3 phage display vectors along with compatible protein expression vectors can be used to generate phage display vectors for antibody diversification.

The mutated DNA provides sequence diversity, and each transformant phage displays one variant of the initial template amino acid sequence encoded by the DNA, leading to a phage population (library) displaying a vast number of different but structurally related amino acid sequences. Due to the well-defined structure of antibody hypervariable regions, the amino acid variations introduced in a phage display screen are expected to alter the binding properties of the binding peptide or domain without significantly altering its overall molecular structure.

In a typical screen, a phage library may be contacted with and allowed to bind one of the foregoing antigens or an epitope thereof. To facilitate separation of binders and non-binders, it is convenient to immobilize the target on a solid support. Phage bearing a CD117-binding moiety can form a complex with the target on the solid support, whereas non-binding phage remain in solution and can be washed away with excess buffer. Bound phage can then liberated from the target by changing the buffer to an extreme pH (pH 2 or pH 10), changing the ionic strength of the buffer, adding denaturants, or other known means.

The recovered phage can then be amplified through infection of bacterial cells, and the screening process can be repeated with the new pool that is now depleted in non-binding antibodies and enriched for antibodies that bind CD117 (e.g., GNNK+CD117). The recovery of even a few binding phage is sufficient to amplify the phage for a subsequent iteration of screening. After a few rounds of selection, the gene sequences encoding the antibodies or antigen-binding fragments thereof derived from selected phage clones in the binding pool are determined by conventional methods, thus revealing the peptide sequence that imparts binding affinity of the phage to the target. During the panning process, the sequence diversity of the population diminishes with each round of selection until desirable peptide-binding antibodies remain. The sequences may converge on a small number of related antibodies or antigen-binding fragments thereof. An increase in the number of phage recovered at each round of selection is an indication that convergence of the library has occurred in a screen.

Example 3. Producing Humanized Antibodies that Bind a Hematopoietic Stem Cell Antigen Non-human antibodies that bind CD117 (e.g., GNNK+CD117) can be humanized, for instance, according to the following procedure. Consensus human antibody heavy chain and light chain sequences are known in the art (see e.g., the "VBASE" human germline sequence database; Kabat et al. Sequences of Proteins of Immunological Interest, Fifth Edition, U.S. Department of Health and Human Services, NIH Publication No. 91-3242, 1991; Tomlinson et al., J. Mol. Biol. 227:776-798, 1992; and Cox et al. Eur. J. Immunol. 24:827-836, 1994, the disclosures of each of which are incorporated herein by reference as they pertain to consensus human antibody heavy chain and light chain sequences. Using established procedures, one of skill in the art can identify the variable domain framework residues and CDRs of a consensus antibody sequence (e.g., by sequence alignment). One can substitute one or more CDRs of the heavy chain and/or light chain variable domains of consensus human antibody with one or more corresponding CDRs of a non-human antibody that binds CD117 (e.g., GNNK+CD117) as described herein in order to produce a humanized antibody. This CDR exchange can be performed using gene editing techniques described herein or known in the art.

One example of a variable domain of a consensus human antibody contains the heavy chain variable domain EVQLVESGGGLVQPGGSLRLSCAASGFTFSDYAM-SWVRQAPGKGLEWVAVISENGSD TYYADSVKGR-FTISRDDSKNTLYLQMNSLRAEDTAVYYCARDRG-GAVSYFDVWGQGT LVTVSS (SEQ ID NO: 7) and the light chain variable domain DIQMTQSPSSLSAS-VGDRVTITCRASQDVSSYLAWYQQKPGKAPKLLI-YAASSLESGVP SRFSGSGSGTDFTLTISSLQPEDFA-TYYCQQYNSLPYTFGQGTKVEIKRT (SEQ ID NO: 8), identified in U.S. Pat. No. 6,054,297, the disclosure of which is incorporated herein by reference as it pertains to human antibody consensus sequences. The CDRs in the above sequences are shown in bold.

To produce humanized antibodies, one can recombinantly express a polynucleotide encoding the above consensus sequence in which one or more variable region CDRs have been replaced with one or more variable region CDR sequences of a non-human antibody that binds CD117 (e.g., GNNK+CD117). As the affinity of the antibody for the hematopoietic stem cell antigen is determined primarily by the CDR sequences, the resulting humanized antibody is expected to exhibit an affinity for the hematopoietic stem cell antigen that is about the same as that of the non-human antibody from which the humanized antibody was derived. Methods of determining the affinity of an antibody for a target antigen include, for instance, ELISA-based techniques described herein and known in the art, as well as surface plasmon resonance, fluorescence anisotropy, and isothermal titration calorimetry, among others.

Example 4. Ability of Anti-CD117 Antibody-Drug Conjugates to Deplete Populations of CD117+ Cells To investigate the ability of anti-CD117 antibody-drug conjugates to kill CD117+ cells, a series of experiments was conducted in which a series of monoclonal antibodies that bind CD117 were conjugated to one of a variety of cytotoxic agents and were subsequently incubated with distinct CD117+ cell lines. Following a defined incubation period, the viability of the cells was assessed by either (i) determining the proportion of cells that cross-react with Annexin V, a phospholipid-binding protein that recognizes phosphatidyl serine so as to identify apoptotic cells, (ii) using the CellTiter-Glo™ assay (Promega, Madison, Wis.), which produces a luminescent signal due to the adenosine triphosphate (ATP)-mediated, luciferase-catalyzed conversion of luciferin to oxyluciferin, thereby detecting the relative concentration of ATP produced by viable cells in culture, or (iii) using flow cytometry. A monoclonal antibody-drug conjugate of the same isotype but that does not bind CD117 was used as a negative control.

To generate the antibody-drug conjugates used in these experiments, monoclonal anti-CD117 antibodies or isotype controls were either bound to Fab fragments conjugated to saporin or were directly conjugated to saporin, monomethyl auristatin E (MMAE), monomethyl auristatin F (MMAF), or α-amanitin.

Figure 2:
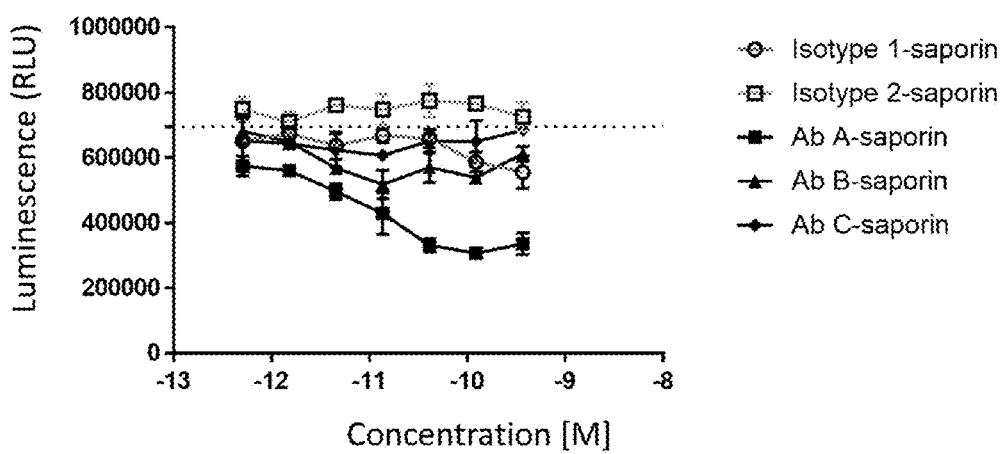
FIG. 2 is a graph demonstrating the effect of various concentrations of anti-CD117 monoclonal antibodies Ab A, Ab B, and Ab C, or isotype-matched negative controls, each conjugated to saporin by way of saporin-conjugated Fab fragments, on the viability of Kasumi-1 cells in vitro. Cell viability was assessed using the CellTiter-Glo™ (Promega, Madison, Wis.) assay kit as described in Example 4, below.
Figure 3:
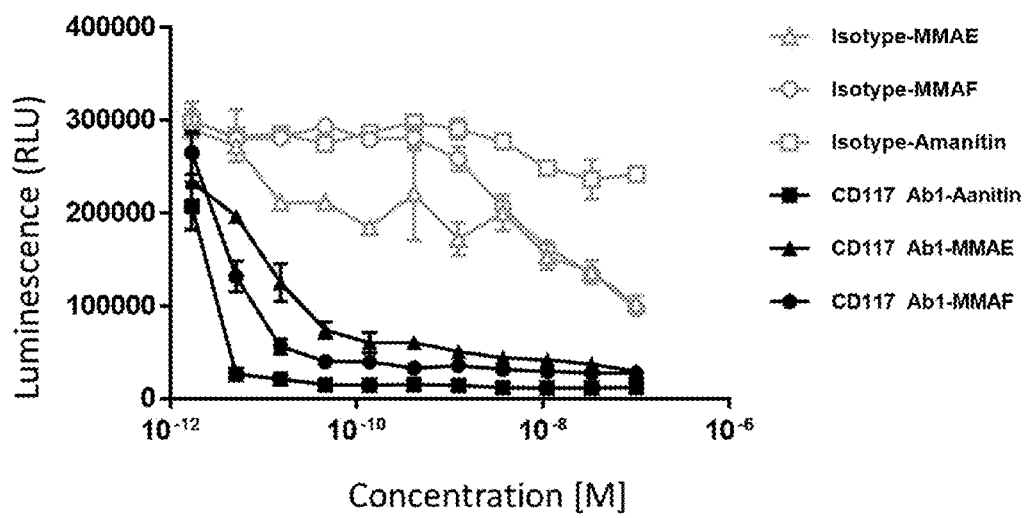
FIG. 3 is a graph demonstrating the effect of various concentrations of anti-CD117 monoclonal antibody or isotype-matched negative controls, each directly conjugated to monomethyl auristatin E (MMAE), monomethyl auristatin F (MMAF), or α-amanitin, on the viability of Kasumi-1 cells in vitro. Cell viability was assessed using the CellTiter-Glo™ assay kit as described in Example 4, below.

The effects of monoclonal antibody-drug conjugates were first assessed on CD117+ Kasumi-1 cells. In one experiment, the cells were incubated with an anti-CD117 antibody or isotype control, bound to saporin-conjugated Fab fragments as described above, for three days, following which time the viability of the cells was assessed by determining Annexin V reactivity. The results of this experiment are shown in FIG. 1. To assess the cell-killing abilities of other anti-CD117 monoclonal antibody-saporin conjugates, a series of monoclonal anti-CD117 antibodies, Ab A, Ab B, and Ab C, were bound to saporin-conjugated Fab fragments in the same fashion and were similarly incubated with Kasumi-1 cells for three days. Following this incubation period, cell viability was determined using the CellTiter-Glo™ assay. The results of this experiment are shown in FIG. 2. To assess the effects of anti-CD117 antibodies conjugated to other cytotoxic agents, the anti-CD117 monoclonal antibody or isotype control directly conjugated to MMAE, MMAF, or α-amanitin was incubated with Kasumi-1 cells for a four-day period, followed which time cell viability was assessed using the CellTiter-Glo™ assay. These results are reported in FIG. 3. Surprisingly, anti-CD117 antibodies conjugated to α-amanitin were found to exhibit a superior ability to kill CD117+ Kasumi-1 cells relative to the various other toxins tested, as anti-CD117 antibody-α-amanitin conjugates depleted Kasumi-1 cells in a dose-dependent manner and with an unexpectedly higher potency than the auristatins and saporin cytotoxins.

Figure 4A:
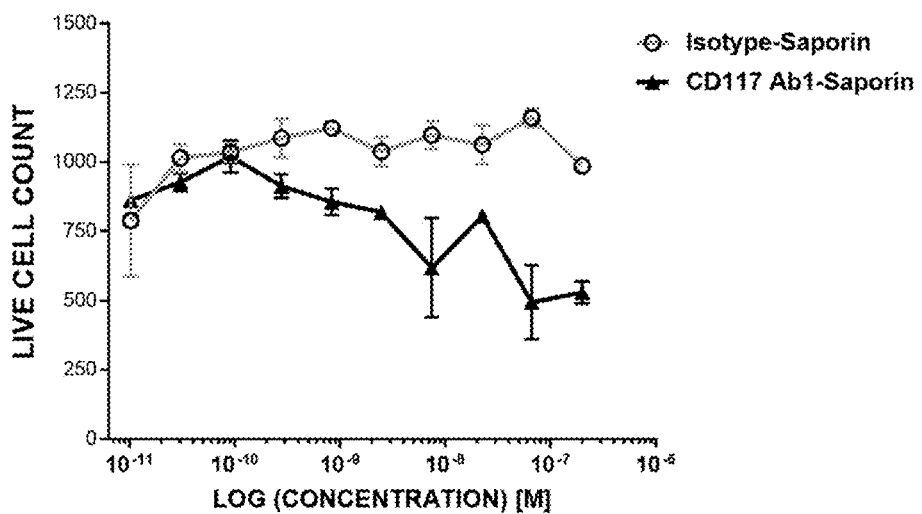
FIG. 4A and FIG. 4B are graphs demonstrating the effect of various concentrations of anti-CD117 monoclonal antibody or isotype-matched negative controls, each conjugated to either saporin or α-amanitin as described in Example 4, below, on the viability of human CD34+ cells in vitro. Cell viability was assessed using flow cytometry (FIG. 4A) or the CellTiter-Glo™ assay kit (FIG. 4B).
Figure 4B:
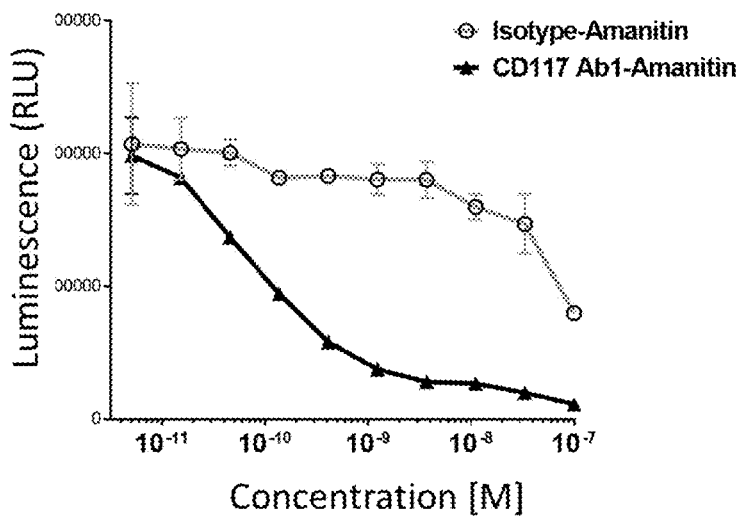
Figure 5A:
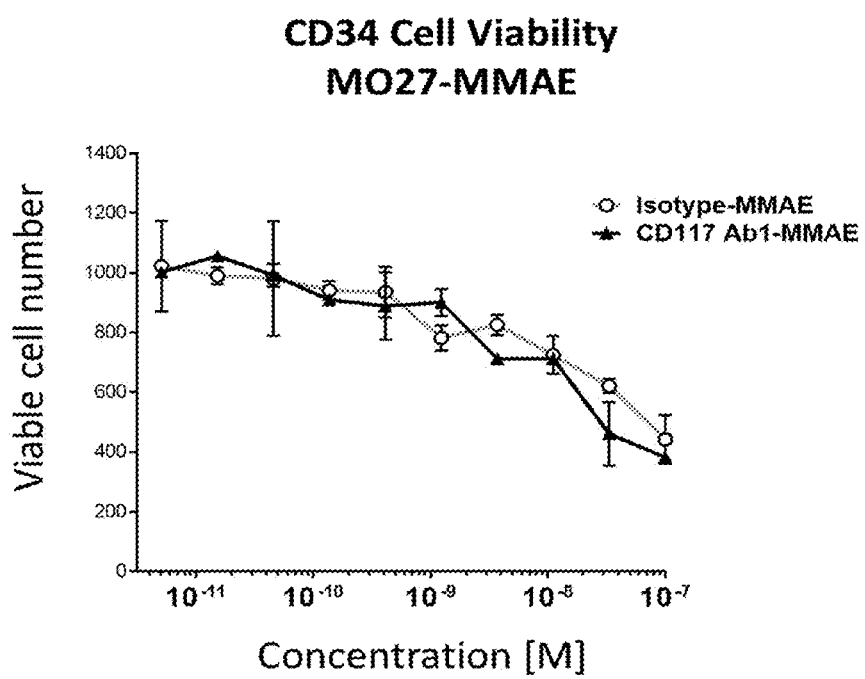
FIG. 5A and FIG. 5B are graphs demonstrating the effect of various concentrations of anti-CD117 monoclonal antibody or isotype-matched negative controls, each directly conjugated to MMAE or MMAF, on the viability of human CD34+ cells in vitro. Cell viability was assessed using flow cytometry.
Figure 5B:
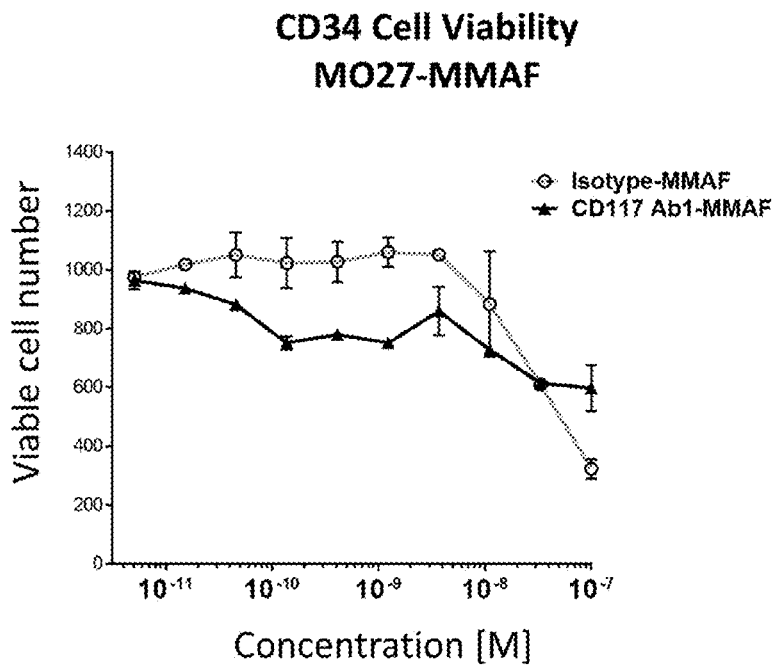

To assess the effects of monoclonal antibody-drug conjugates on CD117+CD34+ cells, an anti-CD117 antibody was directly conjugated to saporin or α-amanitin and was subsequently incubated with CD117+CD34+ cells at increasing concentrations. As negative controls, isotype-matched monoclonal antibodies were bound to saporin-conjugated Fab fragments or were directly conjugated to α-amanitin. Following a five-day incubation period with CD117+CD34+ cells, the viability of the cells was assessed using flow cytometry for those cells treated with saporin conjugates or using the CellTiter-Glo™ assay for cells treated with α-amanitin conjugates. As shown in FIGS. 4A and 4B, anti-CD117 antibodies conjugated to α-amanitin exhibited a surprisingly superior ability to deplete CD117+CD34+ cells, exerting this cell-killing effect in a dose-dependent manner and with a substantially higher potency to a greater extent than monoclonal antibodies bound to saporin. A similar series of experiments was conducted using an anti-CD117 monoclonal antibody or isotype-matched antibody directly conjugated to MMAE and MMAF, which were incubated with CD117+CD34+ cells for six days, following which time cell death was assessed by flow cytometry. As shown in FIGS. 5A and 5B, the anti-CD117 monoclonal antibody-MMAE and -MMAF conjugates did not deplete the test cell population to a greater extent or with a greater potency relative to the isotype-matched control.

Figure 6:
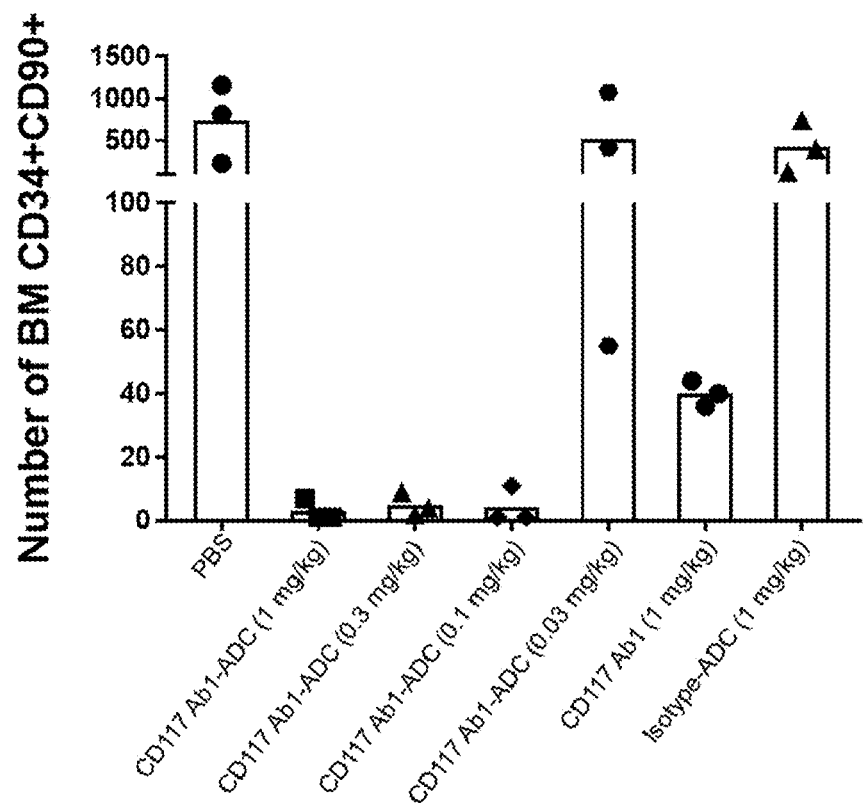
FIG. 6 is a graph demonstrating the effect of various doses of anti-CD117 monoclonal antibody conjugated to α-amanitin, as well as isotype-matched negative control antibody-α-amanitin conjugate and anti-CD117 monoclonal antibody alone, on the viability of human CD34+ cells in NSG mice as described in Example 4, below.

The results of the foregoing experiments demonstrate that not all toxins bound to an anti-CD117 antibody are capable of killing CD117+ cells, and that anti-CD117 antibodies conjugated to α-amanitin exhibit a surprisingly superior capacity for depleting CD117+ cells across distinct cell lines. To investigate the ability of anti-CD117 antibody-α-amanitin conjugates to deplete human cells in vivo that express the hematopoietic stem cell marker CD34, NSG mice engrafted with human CD34+ cells were treated with either PBS buffer, monoclonal anti-CD117 antibody alone, monoclonal anti-CD117 antibody-α-amanitin conjugate, or isotype-matched negative control α-amanitin conjugate by a single intravenous administration. The mice were subsequently observed, and 22 days following the administration, bone marrow was harvested and analyzed to identify human cells, including CD45+ and CD34+ cells. As shown in FIG. 6, anti-CD117 antibodies conjugated to α-amanitin were capable of substantially depleting populations of human CD34+ cells in NSG mice in a dose-dependent manner, while anti-CD117 monoclonal antibody alone and isotype-matched α-amanitin conjugate did not exhibit this phenotype. These results demonstrate that anti-CD117 antibodies conjugated to an amatoxin can be used to deplete a population of hematopoietic stem cells in a subject, for instance, in preparation for hematopoietic stem cell transplant therapy, so as to provide a niche for to which the hematopoietic stem cells may home.

Other Embodiments

All publications, patents, and patent applications mentioned in this specification are incorporated herein by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the invention that come within known or customary practice within the art to which the invention pertains and may be applied to the essential features hereinbefore set forth, and follows in the scope of the claims.

Other embodiments are within the claims.

What is claimed is:

1. A method of depleting a population of CD117+ cells in a human patient, the method comprising administering an effective amount of a conjugate comprising an anti-CD117 monoclonal antibody and an amatoxin, wherein the monoclonal antibody is internalized by a CD117+ cell, wherein the patient does not have an immunodeficiency disorder, and wherein the monoclonal antibody comprises the following complementary determining regions (CDRs):

a CDR-H1 having the amino acid sequence SYWIG (SEQ ID NO: 1)
   a CDR-H2 having the amino acid sequence IIYPGDS-DTRYSPSFQG (SEQ ID NO: 2)
   a CDR-H3 having the amino acid sequence HGRGYN-GYEGAFDI (SEQ ID NO: 3)
   a CDR-L1 having the amino acid sequence RASQGIS-SALA (SEQ ID NO: 4)
   a CDR-L2 having the amino acid sequence DASSLES (SEQ ID NO: 5)
   a CDR-L3 having the amino acid sequence CQQFNSY-PLT (SEQ ID NO: 6), wherein the monoclonal antibody is conjugated to the amatoxin by way of a cysteine residue in the Fc domain of the antibody.

2. The method of claim 1, wherein the amatoxin is selected from the group consisting of, α-amanitin, β-amanitin, γ-amanitin, ε-amanitin, amanin, amaninamide, amanullin, amanullinic acid, and proamanullin.

3. The method of claim 1, wherein the amatoxin is represented by formula (I)

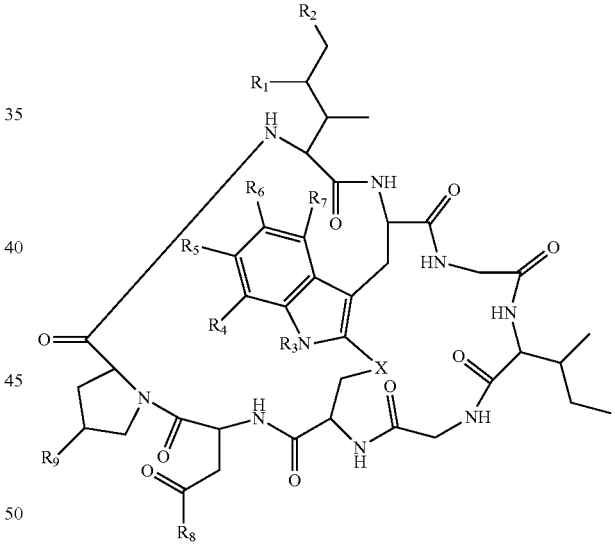

wherein $R_1$ is H, OH, $OR_A$, or $OR_C$;
$R_2$ is H, OH, $OR_B$, or $OR_C$;
$R_A$ and $R_B$, together with the oxygen atoms to which they are bound, combine to form an optionally substituted 5-membered heterocycloalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is substituted $C_1$-$C_6$ alkyl, substituted $C_1$-$C_6$ heteroalkyl, substituted $C_2$-$C_6$ alkenyl, substituted $C_2$-$C_6$ heteroalkenyl, substituted $C_2$-$C_6$ alkynyl, substituted $C_2$-$C_6$ heteroalkynyl, substituted cycloalkyl, substituted heterocycloalkyl, substituted aryl, or substituted heteroaryl;

L is a peptide containing linker; and

Z is a chemical moiety formed from a coupling reaction between a reactive substituent present on L and a reactive substituent present within the antibody or antigen-binding fragment thereof.

4. The method of claim 1, wherein the cysteine residue is introduced by way of a mutation in the Fc domain of the antibody.

5. The method of claim 1, wherein the cysteine residue is naturally occurring in the Fc domain of the antibody.

6. The method of claim 1, wherein the population of CD117+ cells comprises hematopoietic stem cells (HSCs).

7. A method of conditioning a human patient for receiving a hematopoietic stem cell (HSC) transplantation, said method administering an effective amount of a conjugate comprising an anti-CD117 monoclonal antibody and an amatoxin, wherein the monoclonal antibody is internalized by a CD117+ cell, wherein the patient does not have an immunodeficiency disorder, and wherein the monoclonal antibody comprises the following complementary determining regions (CDRs):

a CDR-H1 having the amino acid sequence SYWIG (SEQ ID NO: 1)

a CDR-H2 having the amino acid sequence IIYPGDSDTRYSPSFQG (SEQ ID NO: 2)

a CDR-H3 having the amino acid sequence HGRGYNGYEGAFDI (SEQ ID NO: 3)

a CDR-L1 having the amino acid sequence RASQGISSALA (SEQ ID NO: 4)

a CDR-L2 having the amino acid sequence DASSLES (SEQ ID NO: 5)

a CDR-L3 having the amino acid sequence CQQFNSYPLT (SEQ ID NO: 6), wherein the monoclonal antibody is conjugated to the amatoxin by way of a cysteine residue in the Fc domain of the antibody.

8. The method of claim 7, wherein the amatoxin is selected from the group consisting of α-amanitin, β-amanitin, γ-amanitin, ε-amanitin, amanin, amaninamide, amanullin, amanullinic acid, and proamanullin.

9. The method of claim 7, wherein the amatoxin is represented by formula (I)

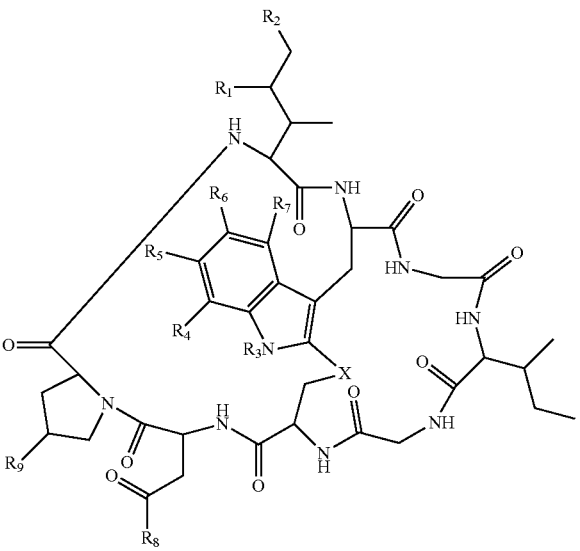

wherein $R_1$ is H, OH, $OR_A$, or $OR_C$;

$R_2$ is H, OH, $OR_B$, or $OR_C$;

$R_A$ and $R_B$, together with the oxygen atoms to which they are bound, combine to form an optionally substituted 5-membered heterocyclolalkyl group;

$R_3$ is H, $R_C$, or $R_D$;

$R_4$, $R_5$, $R_6$, and $R_7$ are each independently H, OH, $OR_C$, $OR_D$, $R_C$, or $R_D$;

$R_8$ is OH, $NH_2$, $OR_C$, $OR_D$, $NHR_C$, or $NR_CR_D$;

$R_9$ is H, OH, $OR_C$, or $OR_D$;

X is —S—, —S(O)—, or —$SO_2$—;

$R_C$ is -L-Z;

$R_D$ is substituted $C_1$-$C_6$ alkyl, substituted $C_1$-$C_6$ heteroalkyl, substituted $C_2$-$C_6$ alkenyl, substituted $C_2$-$C_6$ heteroalkenyl, substituted $C_2$-$C_6$ alkynyl, substituted $C_2$-$C_6$ heteroalkynyl, substituted cycloalkyl, substituted heterocycloalkyl, substituted aryl, or substituted heteroaryl;

L is a peptide containing linker; and

Z is a chemical moiety formed from a coupling reaction between a reactive substituent present on L and a reactive substituent present within the antibody or antigen-binding fragment thereof.

10. The method of claim 7, wherein the human patient has a hematological cancer selected from the group consisting of acute myeloid leukemia, acute lymphoid leukemia, chronic myeloid leukemia, chronic lymphoid leukemia, multiple myeloma, diffuse large B-cell lymphoma, and non-Hodgkin's lymphoma.

11. The method of claim 7, wherein a population of endogenous CD117+ HSCs are depleted following administration of the conjugate.

12. The method of claim 7, further comprising administering an HSC transplant to the human patient.

13. A method of treating a human patient in need of hematopoietic stem cell transplant therapy, said method comprising administering an effective amount of a conjugate comprising an anti-CD117 monoclonal antibody and an amatoxin, wherein the monoclonal antibody is internalized by a CD117+ cell, wherein the patient does not have an immunodeficiency disorder, and wherein the monoclonal antibody comprises the following complementary determining regions (CDRs):

a CDR-H1 having the amino acid sequence SYWIG (SEQ ID NO: 1)

a CDR-H2 having the amino acid sequence IIYPGDSDTRYSPSFQG (SEQ ID NO: 2)

a CDR-H3 having the amino acid sequence HGRGYNGYEGAFDI (SEQ ID NO: 3)

a CDR-L1 having the amino acid sequence RASQGISSALA (SEQ ID NO: 4)

a CDR-L2 having the amino acid sequence DASSLES (SEQ ID NO: 5)

a CDR-L3 having the amino acid sequence CQQFNSYPLT (SEQ ID NO: 6), wherein the monoclonal antibody is conjugated to the amatoxin by way of a cysteine residue in the Fc domain of the antibody.

14. The method of claim 13, wherein the human patient has a hematological cancer.

15. The method of claim 13, wherein the wherein the amatoxin is represented by formula (I)

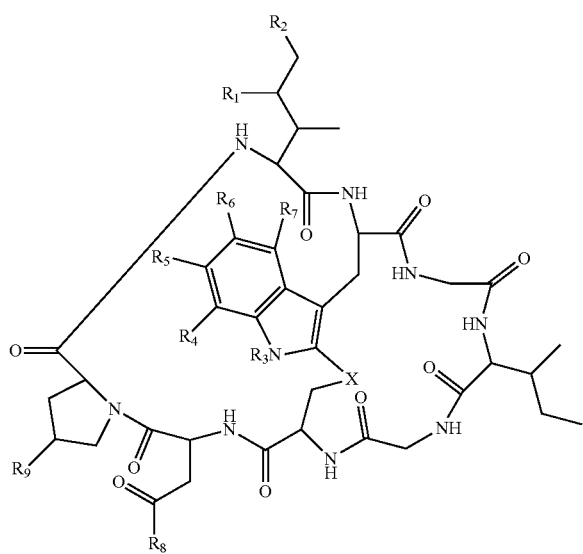

wherein $R_1$ is H, OH, $OR_A$, or $OR_C$;
$R_2$ is H, OH, $OR_B$, or $OR_C$;

$R_A$ and $R_B$, together with the oxygen atoms to which they are bound, combine to form an optionally substituted 5-membered heterocyclolalkyl group;
$R_3$ is H, $R_C$, or $R_D$;
$R_4$, $R_5$, $R_6$, and $R_7$ are each independently H, OH, $OR_C$, $OR_D$, $R_C$, or $R_D$;
$R_8$ is OH, $NH_2$, $OR_C$, $OR_D$, $NHR_C$, or $NR_CR_D$;
$R_9$ is H, OH, $OR_C$, or $OR_D$;
X is —S—, —S(O)—, or —$SO_2$—;
$R_C$ is -L-Z;
$R_D$ is substituted $C_1$-$C_6$ alkyl, substituted $C_1$-$C_6$ heteroalkyl, substituted $C_2$-$C_6$ alkenyl, substituted $C_2$-$C_6$ heteroalkenyl, substituted $C_2$-$C_6$ alkynyl, substituted $C_2$-$C_6$ heteroalkynyl, substituted cycloalkyl, substituted heterocycloalkyl, substituted aryl, or substituted heteroaryl;
L is a peptide containing linker; and
Z is a chemical moiety formed from a coupling reaction between a reactive substituent present on L and a reactive substituent present within the antibody.

16. The method of claim 13, wherein the amatoxin is selected from the group consisting of α-amanitin, β-amanitin, γ-amanitin, ε-amanitin, amanin, amaninamide, amanullin, amanullinic acid, and proamanullin.

* * * * *